US007105634B2

(12) United States Patent
Cheng et al.

(10) Patent No.: US 7,105,634 B2
(45) Date of Patent: Sep. 12, 2006

(54) GENETIC CONSTRUCTS ENCODING CAROTENOID BIOSYNTHETIC ENZYMES

(75) Inventors: Qiong Cheng, Wilmington, DE (US); Kelley C. Norton, Avondale, PA (US); Luan Tao, Claymont, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 407 days.

(21) Appl. No.: 10/358,917

(22) Filed: Feb. 5, 2003

(65) Prior Publication Data

US 2003/0182687 A1    Sep. 25, 2003

Related U.S. Application Data

(60) Provisional application No. 60/355,939, filed on Feb. 11, 2002.

(51) Int. Cl.
| | |
|---|---|
| C07H 21/04 | (2006.01) |
| C12N 9/06 | (2006.01) |
| C12N 1/20 | (2006.01) |
| C12N 15/00 | (2006.01) |
| C12N 1/15 | (2006.01) |
| C12N 1/19 | (2006.01) |
| C12N 5/04 | (2006.01) |

(52) U.S. Cl. .................. 530/23.2; 435/191; 435/252.3; 435/252.33; 435/254.1; 435/254.2; 435/419

(58) Field of Classification Search ..................... None
See application file for complete search history.

(56) References Cited

U.S. PATENT DOCUMENTS

| | | | |
|---|---|---|---|
| 5,182,208 | A | 1/1993 | Johnson et al. |
| 5,429,939 | A | 7/1995 | Misawa et al. |
| 5,466,599 | A | 11/1995 | Jacobson et al. |
| 5,530,188 | A | 6/1996 | Ausich et al. |
| 5,530,189 | A | 6/1996 | Ausich et al. |
| 5,545,816 | A | 8/1996 | Ausich et al. |
| 5,656,472 | A | 8/1997 | Ausich et al. |
| 5,691,190 | A | 11/1997 | Girard et al. |
| 5,972,642 | A | 10/1999 | Fleno et al. |
| 6,015,684 | A | 1/2000 | Jacobson et al. |
| 6,124,113 | A | 9/2000 | Hohmann et al. |
| 2003/0003528 | A1 | 1/2003 | Brzostowics et al. |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
UniProt_03 database Acession No. DHAB_BACSU Nov. 1, 1997 from Boch et al., Synthesis of the osmoprotectant glycine betaine in Bacillus subtilis: characterization of the gbsAB genes. J Bacteriol. Sep. 1996;178(17):5121-9. Alignment with SEQ ID No. 6.*

Boch et al., Synthesis of the osmoprotectant glycine betaine in Bacillus subtilis: characterization of the gbsAB genes. J Bacteriol. Sep. 1996;178(17):5121-9.*
Lassner et al., Directed molecular evolution in plant improvement. Curr Opin Plant Biol. Apr. 2001;4(2):152-6. Review.*
Nelis and Leenheer,Microbial sources of carotenoid pigments used in foods and feeds, Appl. Bacteriol. 70: 181-191, 1991.
Kushwaha, S.C. et al., Isolation and identification of dehydrosqualene and C40 Carotenoid Pigments in Halobacterium Cutirubrum, Biochim. Biophys Acta. vol. 260: pp. 492-506, 1972.
Armstrong, Eubacteria Show Their True Colors: Genetics of Carotenoid Pigment Biosyntehsis from Microbes to Plants, J. Bact. vol. 176: pp. 4795-4802, 1994.
Armstrong, Genetics of Eubacterial Carotenoid Biosynthesis: A Colorful Tale, Annu. Rev. Microbiol. vol. 51: pp. 629-659, 1997.
Farmer W. R. et al., Precursor Balancing for Metabolic Engineering of Lycopene Production in *Escherichia coli*, Biotechnol. Prog. vol. 17: pp. 57-61, 2001.
Wang C. et al., Directed Evolution of Metabolically Engineered *Escherichia coli* for Cartenoid Production, Biotechnol. Prog. vol. 16: pp. 922-926, 2000.
Misawa, N. et al., Metabolic engineering for the production of carotenoids in non-carotenogenic bacteria and yeasts, J. Biotechnol. vol. 59: pp. 169-181, 1998.
Shimada, H. et al., Increased Carotenoid Production by the Food Yeast *Candida utilis* through Metabolic Engineering of the Isopremoid Pathway. Appl. Environ. Microbiol. vol. 64: pp. 2676-2680, 1998.
Albrect, M. et al., Metabolic engineering of the terpenoid biosynthetic pathway of *Escherichia coli* for production of the carotenoids □-carotene and zeaxanthin, Biotechnol. Lett. vol. 21: pp. 791-795, 1999.
Miura, Y. et al.,Production of the Carotenoids Lycopene □-Carotene, and Astaxanthin in the Food yeast *Candida utilis*, Appl. Environ. Microbiol. vol. 64: 1226-1229, 1998.
Kleinig, H. et al., New C30-Carotenoic Acid Glucosyl Esters from *Pseudomonas rhodos*. Z. Naturforsch 34c: pp. 181-185, 1979.
Kleinig, On the Biosynthesis of C30 Carotenoic Acid Glucosyl Esters in *Pseudomonas rhodos*. Analysis of car-Mutants, Z. Naturforsch 37c: pp. 758-760, 1982.
Taylor, R. F. et al., Triterpenoid Carotenoids and Related Lipids, J. Biochem. vol. 139: 751-760, 1974.
Taylor, R. F., Bacterial Triterpenoids, Microbiol. Rev. vol. 48: pp. 181-198, 1984.
Takaichi, S. et al., The major carotenoid in all known species of heliobacteria is the C30 carotenoid 4,4'-diaponeurosporene, not neurosporene. Arch. Microbiol. vol. 168: pp. 277-281, 1997.
Marshall, J. H. et al., Pigments of *Staphylococcus aureus*, a Series of Triterpoenoid Carotenoids, J. Bacteriol., vol. 147: pp. 900-913, 1981.
Raisig et al., Functional properties of diapophytoene and related desaturases of C30 and C40 carotenoid biosynthetic pathways, Biochim. Biophys. Acta. vol. 1533: pp. 164-170, 2001.

(Continued)

Primary Examiner—Sheridan L. Swope

(57) ABSTRACT

Genes isolated from *Methylomonas* sp. 16a have been determined to play a role in the carotenoid biosynthetic pathway. Specifically, crtN2 gene has the ability to produce omega-aldehyde functional groups on carotenogenic substrates, while the ald gene produced omega carboxyl functional groups. These genes will be useful for production of high levels of functionalized carotenoid compounds, especially those produced in microorganisms which metabolize single carbon substrates.

8 Claims, 9 Drawing Sheets

OTHER PUBLICATIONS

Marshall, J. H. et al., Proposed Pathway of Triterpenoid Carotenoid biosynthesis in *Staphylococcus aureus*: Evidence from a Study of Mutants, J. Bacteriol. vol. 147: pp. 914-919, 1981.

Genbank Accession No. X73889, Wieland, B et al., *Staphylococcus aureus*, Mar. 10, 2001.

Kuroda et al., Access No. AP003137, *Staphyloccus aureus* subsp. aureus N315, Jan. 11, 2003.

Kuroda et al., *Staphylococcus aureus* subsp. aureus Mu50. Acc. No. AP003365, Feb. 7, 2002.

Raisig, A. et al., 4,4'Diapophytoene Desaturase: Catalytic Properties of an Enzyme from the C30 Carotenoid Pathway of *Staphylococcus aureus*, J. Bacteriol. vol. 181(19): pp. 6148-6187, 1999.

Tippelt, A. et al., Squalene-hopene cyclase from *Methylococcus capsulantus* (bath): a bacaterium producing hopanoids and steroids, Biochim. Biophys. Acta. 1391: pp. 223-232, 1998.

Xiong, J. et al., Tracking molecular evolution of photosynthesis by characterization fo a major photosynthesis gene cluster from *Heliobacillus mobilis*, P. N. A. S. vol. 95, 6685, pp. 14851-14856, 1998.

Lin, X. et al., *Arabidopsis thaliana*, Jan. 19, 2001, Cession No. AAG50992, Unpublished bg/aag50992.1/ac036.

Kuroda, M. et al., Whole genome sequencing of meticillin-resistant *Staphylococcus aureus*, Lancet 397. 9264, pp. 1225-1240, 1998.

Nakashima, T., et al., Cloning, Expression, and characterization of cDNAs encoding *Arabidopsis thaliana* squalene synthase, PNAS, vol. 92: pp. 2328-2332, 1995.

Weiland et al., Genetic and BiochemicalAnalyses of the Biosynthesis of theYellow Carotenoid 4,4'-Diaponeurosporene of *Staphylococcus aureus*, Journal of Bacteriology, Dec. 1994, 7719-7726.

Merkulov et al., Cloning and characterization of the *Yarrowia lipolytica* squalene synthase (SQSI) gene and functional complementation of the *Saccharomyces cerevisiae* erg9 mutation, Yeast, vol. 16:pp. 197-206, 2000.

Umeno et al., Evolution of the C30- Carotenoid Synthase CrtM for unction in a C40 Pathway. Journal of Bacteriology, Dec. 2002, pp. 6690-6699, vol. 184, No. 23.

* cited by examiner

FIG. 1B

Continued from Fig. 1A

C₃₀ Synthesis sqs,crtM → Diapophytoene → crtN,crtN2ald → → → Lower Carotenoid Biosynthetic Pathway

C₄₀ Synthesis crtE → Geranyl-geranyl pyrophosphate → crtB → Phytoene → CrtIyZxO → → Lycopene, B-carotene, Zeaxanthin-B-D-diglycoside, Astaxanthin, etc

GENETIC CONSTRUCTS ENCODING CAROTENOID BIOSYNTHETIC ENZYMES

This application claims the benefit of U.S. Provisional Application No. 60/355,939 filed Feb. 11, 2002.

FIELD OF THE INVENTION

This invention is in the field of microbiology. More specifically, this invention pertains to nucleic acid fragments encoding enzymes useful for microbial production of functionalized carotenoid compounds.

BACKGROUND OF THE INVENTION

Carotenoids represent one of the most widely distributed and structurally diverse classes of natural pigments, producing pigment colors of light yellow to orange to deep red. Eye-catching examples of carotenogenic tissues include carrots, tomatoes, red peppers, and the petals of daffodils and marigolds. Carotenoids are synthesized by all photosynthetic organisms, as well as some bacteria and fungi. These pigments have important functions in photosynthesis, nutrition, and protection against photooxidative damage. For example, animals do not have the ability to synthesize carotenoids but must instead obtain these nutritionally important compounds through their dietary sources.

Industrially, only a few carotenoids are used for food colors, animal feeds, pharmaceuticals, and cosmetics, despite the existence of more than 600 different carotenoids identified in nature. This is largely due to difficulties in production. Presently, most of the carotenoids used for industrial purposes are produced by chemical synthesis; however, these compounds are very difficult to make chemically (Nelis and Leenheer, *Appl. Bacteriol.* 70:181–191 (1991)). Natural carotenoids can either be obtained by extraction of plant material or by microbial synthesis, but only a few plants are widely used for commercial carotenoid production and the productivity of carotenoid synthesis in these plants is relatively low. As a result, carotenoids produced from these plants are very expensive.

Structurally, the most common carotenoids are 40-carbon ($C_{40}$) terpenoids; however, carotenoids with only 30 carbon atoms ($C_{30}$; diapocarotenoids) are detected in some species. Biosynthesis of each of these types of carotenoids are derived from the isoprene biosynthetic pathway and its five-carbon universal isoprene building block, isopentenyl pyrophosphate (IPP). This biosynthetic pathway can be divided into two portions: 1) the upper isoprenoid pathway, which leads to the formation of farnesyl pyrophosphate (FPP); and 2) the lower carotenoid biosynthetic pathway, comprising various crt genes which convert FPP into long $C_{30}$ and $C_{40}$ carotenogenic compounds characterized by a long central chain of conjugated double bonds. It is the degree of the carbon backbone's unsaturation, conjugation and isomerization that determines the specific carotenoids' unique absorption characteristics and colors.

Various other crt genes are known, which enable the intramolecular conversion of linear $C_{30}$ and $C_{40}$ compounds to produce numerous other functionalized carotenoid compounds by: (i) hydrogenation, (ii) dehydrogenation, (iii) cyclization, (iv) oxidation, (v) esterification/glycosylation, or any combination of these processes.

Finally, *Halobacterium cutirubrum* is known to produce both $C_{40}$ and $C_{50}$ carotenoids, as well as a $C_{30}$ diapophytoene (Kushwaha, S. C., et al., *Biochim. Biophys. Acta.* 260: 492–506 (1972)). Other desaturases are likely to soon be developed in laboratories through mutational techniques, to create completely novel carotenoid pathways, up to $C_{80}$. These large carotenoids can potentially undergo many desaturation steps and generate large chromophores for purple or blue-purple pigmentation. Such novel carotenoids have potential applications as strong antioxidants or colorants for foods and cosmetics.

The genetics of $C_{40}$ carotenoid pigment biosynthesis has been extremely well studied in the Gram-negative pigmented bacteria of the genera *Pantoea*, formerly known as *Erwinia*. In both *E. herbicola* EHO-10 (ATCC 39368) and *E. uredovora* 20D3 (ATCC 19321), the crt genes are clustered in two genetic units, crt Z and crt EXYIB (U.S. Pat. No. 5,656,472; U.S. Pat. No. 5,545,816; U.S. Pat. No. 5,530,189; U.S. Pat. No. 5,530,188; U.S. Pat. No. 5,429,939). These genes have subsequently been sequenced and identified in a suite of other species of bacterial, fungal, plant and animal origin. Several reviews discuss the genetics of carotenoid pigment biosynthesis, such as those of Armstrong (*J. Bact.* 176: 4795–4802 (1994); *Annu. Rev. Microbiol.* 51:629–659 (1997)).

The abundant knowledge concerning the genetics of $C_{40}$ biosynthesis has permitted production of a number of natural $C_{40}$ carotenoids from genetically engineered microbial sources. Examples include:

1.) Lycopene (Farmer W. R. and J. C. Liao. *Biotechnol. Prog.* 17: 57–61(2001); Wang C. et al., *Biotechnol Prog.* 16: 922–926 (2000); Misawa, N. and H. Shimada. *J. Biotechnol.* 59: 169–181 (1998); Shimada, H. et al. *Appl. Environ. Microbiol.* 64:2676–2680 (1998));
2.) β-carotene (Albrecht, M. et al., *Biotechnol. Lett.* 21: 791–795 (1999); Miura, Y. et al., *Appl. Environ. Microbiol.* 64:1226–1229 (1998); U.S. Pat. No. 5,691,190);
3.) Zeaxanthin (Albrecht, M. et al., *Biotechnol. Lett.* 21: 791–795 (1999); Miura, Y. et al., *Appl. Environ. Microbiol.* 64:1226–1229 (1998)); and
4.) Astaxanthin (U.S. Pat. No. 5,466,599; U.S. Pat. No. 6,015,684; U.S. Pat. No. 5,182,208; U.S. Pat. No. 5,972,642).

Genes encoding various elements of the lower $C_{40}$ carotenoid biosynthetic pathway have been cloned and expressed in various microbes (U.S. Pat. No. 5,656,472; U.S. Pat. No. 5,545,816; U.S. Pat. No. 5,530,189; U.S. Pat. No. 5,530,188; U.S. Pat. No. 5,429,939; U.S. Pat. No. 6,124,113).

Despite abundant knowledge and understanding of the $C_{40}$ carotenoid pathway, $C_{30}$ pigment biosynthesis is both less well understood and less prevalent in nature. Early studies by Kleinig, H. et al. (*Z. Naturforsch* 34c: 181–185 (1979); *Z. Naturforsch* 37c: 758–760 (1982)) examined the structure of $C_{30}$ carotenoic acid glucosyl esters produced in *Pseudomonas rhodos* (subsequently renamed *Methylobacterium rhodinum*) and the biosynthesis of those compounds, according to analysis of mutants. To date, presence of diapocarotenoids has been discovered in *Streptococcus faecium* (Taylor, R. F. and B. H. Davies. *J. Biochem.* 139:751–760 (1974)), *M. rhodinum* (Kleinig, H. et al., supra; Taylor, R. F. *Microbiol. Rev.* 48:181–198 (1984)), genera of the photosynthetic heliobacteria (Takaichi, S. et al. *Arch. Microbiol.* 168: 277–281 (1997)), and *Staphylococcus aureus* (Marshall, J. H., and G. J. Wilmoth. *J. Bacteriol.*, 147:900–913 (1981)). All appear to have a diapophytoene precursor, from which all subsequent $C_{30}$ compounds are produced.

The relevant genes responsible for $C_{30}$ carotenoid pigment biosynthesis are known to include crtM and crtN in *Staphylococcus aureus*. The diapophytoene desaturase CrtN can function to some extent in the $C_{40}$ pathway, and the phytoene desaturase CrtI of the $C_{40}$ carotenoids can also work in the $C_{30}$ pathway (Raisig and Sandmann, *Biochim. Biophys. Acta*, 1533:164–170 (2001)). Investigators J. H. Marshall and G. J. Wilmonth (*J. Bacteriol.* 147:914–919 (1981)) suggest that mixed-function oxidases are responsible for the introduction of oxygen functions to produce the aldehyde and carboxylic acid of 4,4-diaponeurosporene. However, genes responsible for the addition of functionality to the terminal methyl group of the linear carotenoid molecule have not yet been identified, despite characterization of the resulting carotenoids. Genes in other organisms that produce $C_{30}$ carotenoids have not been identified.

It is clear that scientific understanding has yet to reveal all of nature's untapped diversity, in order to industrially duplicate the wide spectrum of carotenoids that can be readily produced by nature. In light of these needs, the problem to be solved is to isolate and functionally characterize the nucleic acid sequences of those genes involved in $C_{30}$ carotenoid biosynthesis in *Methylomonas* for their use in carotenoid production. Although some of the genes involved in the $C_{30}$ carotenoid biosynthetic pathway are known in some organisms, understanding of the pathway is not complete. Genes involved in the $C_{30}$ carotenoid biosynthesis of methylotrophic bacteria are not described in the existing literature, despite the existence of many pigmented methylotrophic and methanotrophic bacteria. Further, it is necessary to gain functional knowledge of reactions catalyzed by carotenoid enzymes and identify novel carotenoid genes.

Applicants have solved the stated problem by isolating and functionally characterizing three unique open reading frames encoding the enzymes crtN, ald, and crtN2 from a *Methylomonas* sp. strain 16a. These genes will aid in synthesis of carotenoids beyond what is "known" in nature, to enable industrial synthesis and high levels of production of uniquely functionalized $C_{30}$–$C_{80}$ carotenoid compounds.

SUMMARY OF THE INVENTION

The invention provides an isolated nucleic acid molecule encoding a carotenoid biosynthetic enzyme, selected from the group consisting of:
a) an isolated nucleic acid molecule encoding the amino acid sequence as set forth in SEQ ID NO:2;
b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or an isolated nucleic acid molecule that is complementary to (a) or (b).

Additionally the invention provides an isolated nucleic acid molecule encoding a carotenoid biosynthetic enzyme, selected from the group consisting of:
a) an isolated nucleic acid molecule encoding the amino acid sequence as set forth in SEQ ID NO:6;
b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or an isolated nucleic acid molecule that is complementary to (a) or (b).

In a specific embodiment the invention provides an isolated nucleic acid molecule comprising a first nucleotide sequence encoding a polypeptide of at least 363 amino acids that has at least 60% identity based on the Smith-Waterman method of alignment when compared to a polypeptide having the sequence as set forth in SEQ ID NO:2 or a second nucleotide sequence comprising the complement of the first nucleotide sequence, wherein said enzyme has squalene dehydrogenase activity.

In similar fashion the invention provides an isolated nucleic acid molecule comprising a first nucleotide sequence encoding a polypeptide of at least 530 amino acids that has at least 33% identity based on the Smith-Waterman method of alignment when compared to a polypeptide having the sequence as set forth in SEQ ID NO:6 or a second nucleotide sequence comprising the complement of the first nucleotide sequence, wherein said enzyme has aldehyde dehydrogenase activity.

In addition the invention provides polypeptides encoded by the nucleic acid sequence of the invention as well as genetic chimera and host cells comprising the same.

In another preferred embodiment the invention provides a method of obtaining a nucleic acid molecule encoding a carotenoid biosynthetic enzyme comprising:
a) probing a genomic library with the nucleic acid molecule of the present invention;
b) identifying a DNA clone that hybridizes with the nucleic acid molecule of the present invention; and
c) sequencing the genomic fragment that comprises the clone identified in step (b), wherein the sequenced genomic fragment encodes a carotenoid biosynthetic enzyme.

Similarly the invention provides a method of obtaining a nucleic acid molecule encoding a carotenoid biosynthetic enzyme comprising:
a) synthesizing at least one oligonucleotide primer corresponding to a portion of the sequence selected from the group consisting of SEQ ID NOs:1 and 5; and
b) amplifying an insert present in a cloning vector using the oligonucleotide primer of step (a);

wherein the amplified insert encodes a portion of an amino acid sequence encoding an carotenoid biosynthetic enzyme.

In a preferred embodiment the invention provides a method for the production of an omega-aldehyde functionalized carotenoid compound comprising:
a) providing a conjugated polyene carotenoid substrate having the general formula:

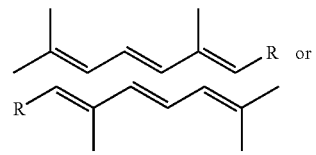

wherein R is the remaining length of the conjugated polyene carbon skeleton;
b) contacting the substrate of (a) with a polypeptide encoded by an isolated nucleic acid molecule selected from the group consisting of:
1) an isolated nucleic acid molecule encoding the amino acid sequence selected from the group consisting of SEQ ID NOs:8 and 14;
2) an isolated nucleic acid molecule that hybridizes with (1) under the following hybridization conditions: 0.1×SSC, 0.1% SDS, 65° C. and washed with 2×SSC, 0.1% SDS followed by 0.1×SSC, 0.1% SDS; or an isolated nucleic acid molecule that is complementary to (1) or (2)
wherein the conjugated polyene carotenoid substrate becomes aldehyde functionalized at the omega carbon.

In an alternate embodiment the invention provides a method for the production of an omega-carboxyl functionalized carotenoid compound comprising:
a) providing a conjugated polyene carotenoid substrate having the general formula: OHC—R or R—CHO wherein R is the remaining length of the conjugated polyene carbon skeleton;
b) contacting the substrate of (a) with a polypeptide of the invention;

wherein the conjugated polyene carotenoid becomes carboxyl functionalized at the omega carbon.

In a specific preferred embodiment the invention provides a method for the production of an omega-carboxyl functionalized carotenoid compound comprising:
(a) providing a transformed C1 metabolizing host cell comprising:
  (i) a conjugated polyene carotenoid substrate having the general formula: OHC—R or R—CHO wherein R is the remaining length of the conjugated polyene carbon skeleton;
  (ii) an isolated nucleic acid molecule encoding the polypeptides of the invention under the control of suitable regulatory sequences;
(b) contacting the host cell of step (a) under suitable growth conditions with an effective amount of a C1 carbon substrate, whereby the polypeptides of the invention are expressed and wherein the conjugated polyene carotenoid substrate becomes carboxyl functionalized at the omega carbon.

In an alternate embodiment the invention provides a method for the production of an omega-aldehyde functionalized carotenoid compound comprising:
(a) providing a transformed C1 metabolizing host cell comprising:
  (i) a conjugated polyene carotenoid substrate having the general formula:

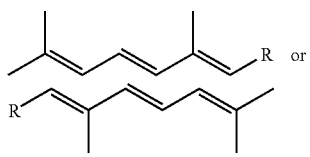

wherein R is the remaining length of the conjugated polyene carbon skeleton;
  (ii) an isolated nucleic acid molecule selected from the group consisting of
    1) an isolated nucleic acid molecule encoding the amino acid sequence selected from the group consisting of SEQ ID NOs:8 and 14;
    2) an isolated nucleic acid molecule that hybridizes with (1) under the following hybridization conditions: 0.1×SSC, 0.1% SDS, 65° C. and washed with 2×SSC, 0.1% SDS followed by 0.1×SSC, 0.1% SDS;
  under the control of suitable regulatory sequences;
(b) contacting the host cell of step (a) under suitable growth conditions with an effective amount of a C1 carbon substrate whereby the isolated nucleic acid molecule is expressed and wherein the conjugated polyene carotenoid substrate becomes aldehyde functionalized at the omega carbon.

In another preferred embodiment the invention provides a method for the production of either an omega-aldehyde functionalized carotenoid compound or an omega-carboxyl functionalized carotenoid compound in a methanotroph where the methanotroph:
(a) grows on a C1 carbon substrate selected from the group consisting of methane and methanol; and
(b) comprises a functional Embden-Meyerhof carbon pathway, said pathway comprising a gene encoding a pyrophosphate-dependent phosphofructokinase enzyme.

In another embodiment the invention provides a method for the production of $C_{30}$ carotenoid compounds comprising:
a) providing a transformed host cell comprising:
  (i) suitable levels of isopentyl pyrophate; and
  (ii) a set of carotenoid biosynthetic genes having the nucleotide sequences as set forth in SEQ ID NO:1, 3, 5, 7, 9, 11, and 13, wherein said genes are operably linked to suitable regulatory sequences; and
b) growing the transformed host cell of (a) under conditions whereby a $C_{30}$ carotenoid compound is produced.

In an additional embodiment the invention provides a method of regulating carotenoid biosynthesis in an organism comprising over-expressing at least one carotenoid gene selected from the group consisting of SEQ ID NOs: SEQ ID NO:1, 3, 5, 7, 9, 11, and 13 in an organism such that the carotenoid biosynthesis is altered in the organism.

BRIEF DESCRIPTION OF THE DRAWINGS SEQUENCE DESCRIPTIONS AND THE BIOLOGICAL DEPOSITS

FIG. 2A shows proposed pathways for $C_{30}$ carotenoid biosynthesis in *Methylomonas* sp. 16a.

Figure 1A:
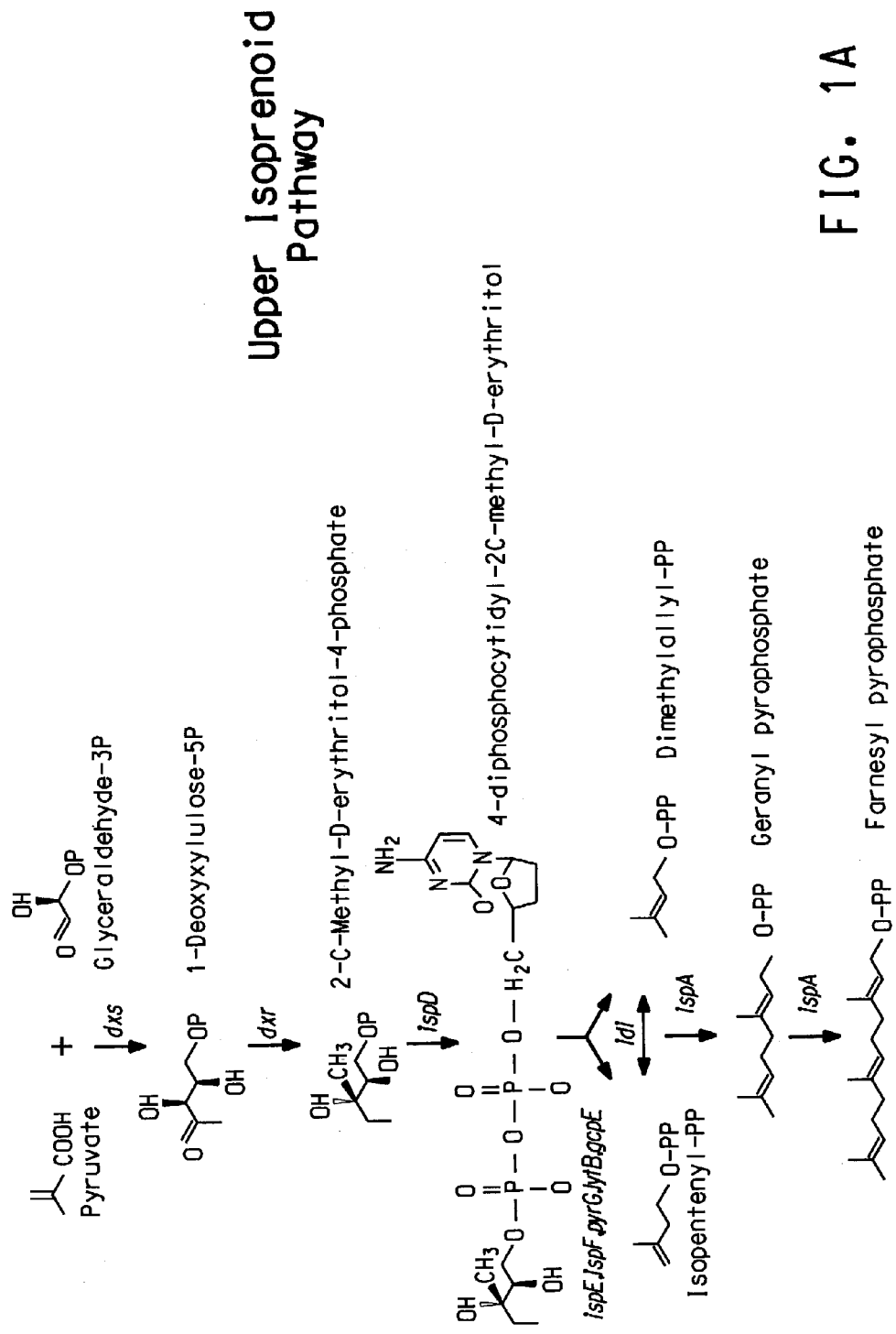
FIG. 1 shows the upper isoprenoid pathway and the lower $C_{30}$ and $C_{40}$ carotenoid pathways.

FIG. 3 schematically illustrates the organization of the crtN gene clusters in *Methylomonas* sp. 16a (A) and *Staphylococcus aureus* NCTC 8325 (ATCC 35556) (B).

FIG. 4 shows the absorption spectra of the $C_{30}$ carotenoids in *E. coli* containing the wild type *Methylomonas* crtN gene cluster (A) or the cluster with transposon insertions designated CrtN⁻ (B), Ald⁻ (C) and CrtN2⁻ (D).

Thenvention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1–14 are full-length genes or proteins as identified in Table 1.

TABLE 1

Summary of Gene and Protein SEQ ID Numbers

| Description | Organism | SEQ ID Nucleic acid | SEQ ID Peptide |
|---|---|---|---|
| Sqs | *Methylomonas* sp.16a | 1 | 2 |
| CrtN | *Methylomonas* sp.16a | 3 | 4 |
| Ald | *Methylomonas* sp.16a | 5 | 6 |
| CrtN2 | *Methylomonas* sp.16a | 7 | 8 |
| CrtM | *Staphylococcus aureus* | 9 | 10 |
| CrtN | *Staphylococcus aureus* | 11 | 12 |
| CrtN2 | *Staphylococcus aureus* | 13 | 14 |

SEQ ID NOs:15 and 16 encode primers crtM_F/Staphyl and crtM_R/Staphyl for amplification of crtM from *S. aureus*.

SEQ ID NOs:17 and 18 encode primers sqs_F/16a and sqs_R/16a for amplification of sqs from *Methylomonas* 16a.

SEQ ID NOs:19 and 20 encode primers crtN_FL and crtN_RL for amplification of the crtN ald crtN2 gene cluster from *Methylomonas* 16a.

SEQ ID NO:21 encodes primer crtN_R, used for PCR screening of transposon insertions.

SEQ ID NOs:22 and 23 encode primers crtN2_F/Staphyl and crtN2_R/NCTC8325, used for amplification of crtN2 from *S. aureus*.

SEQ ID NOs:24 and 25 encode primers crtM_F/NCTC and crtN_R/NCTC for amplification of the crtM crtN gene cluster of *S. aureus*.

SEQ ID NOs:26 and 27 encode primers crtN2_F3/16a and crtN2_R/16a for amplification of the *Methylomonas* 16a crtN2 gene.

SEQ ID NO:28 encodes primer crtN2_F/NCTC, used for amplification of the *S. aureus* crtN2 gene.

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
|---|---|---|
| *Methylomonas* 16a | ATCC PTA 2402 | Aug. 22, 2000 |

DETAILED DESCRIPTION OF THE INVENTION

The genes of this invention and their expression products are useful for the creation of recombinant organisms that have the ability to produce various functionalized carotenoid compounds. Nucleic acid fragments encoding the crtN, crtN2, sqs and ald enzymes have been isolated from a strain of *Methylomonas* 16a and identified by comparison to public databases containing nucleotide and protein sequences using the BLAST and FASTA algorithms well known to those skilled in the art. A gene homologous to crtN2 has also been identified and characterized from *Staphylococcus aureus*. The instant genes have been expressed in *E. coli* as well as a preferred methanotroph (*Methylomonas* 16a, ATCC PTA 2402) for the production of $C_{30}$ carotenoids.

There is a general practical utility for microbial production of carotenoid compounds, as these compounds are very difficult to make chemically (Nelis and Leenheer, *Appl. Bacteriol.* 70:181–191 (1991)). Most carotenoids have strong color and can be viewed as natural pigments or colorants. Furthermore, many carotenoids have potent antioxidant properties and thus inclusion of these compounds in the diet is thought to be healthful. Well-known examples of $C_{40}$ carotenoids are β-carotene and astaxanthin.

In the present invention the discovery of crtN2 and ald genes, which enable the functionalization of the omega-carbon of a carotenoid molecule to yield an aldehyde or carboxyl group, is particularly useful as directed synthesis of carotenoid molecules containing this functionalization is now possible. The genes have utility with carotenoid molecules of various lengths, e.g., from $C_{30}$ and $C_{80}$. The ability to produce these compounds in methanotrophs has an added advantage as a number of these organisms have the inherent capacity to produce $C_{30}$ carotenoids in addition to single cell protein, a component in animal feeds. The genes and gene sequences described herein enable one to engineer the production of a variety of healthful carotenoids directly into the single cell protein product derived from *Methylomonas* 16a. This aspect makes this strain or any methanotrophic strain into which these genes are incorporated or engineered a more desirable production host for animal feed due to the presence of carotenoids which are known to add desirable pigmentation and health benefits to the feed.

Definitions

In this disclosure, a number of terms and abbreviations are used. The following definitions are provided.

"Open reading frame" is abbreviated ORF.

"Polymerase chain reaction" is abbreviated PCR.

The term "isoprenoid compound" refers to compounds formally derived from isoprene (2-methylbuta-1,3-diene; $CH_2=C(CH_3)CH=CH_2$), the skeleton of which can generally be discerned in repeated occurrence in the molecule. These compounds are produced biosynthetically via the isoprenoid pathway beginning with isopentenyl pyrophosphate (IPP) and formed by the head-to-tail condensation of isoprene units, leading to molecules which may be—for example—of 5, 10, 15, 20, 30, or 40 carbons in length.

The term "carotenoid biosynthetic pathway" refers to those genes comprising members of the upper isoprenoid pathway and/or lower carotenoid pathway of the present invention as illustrated in FIG. 1.

The terms "upper isoprenoid pathway" and "upper pathway" will be use interchangeably and will refer the enzymes involved in converting pyruvate and glyceraldehyde-3-phosphate to farnesyl pyrophosphate (FPP). These enzymes include, but are not limited to: the "dxs" gene (encoding 1-deoxyxylulose-5-phosphate synthase); the "dxr" gene (encoding 1-deoxyxylulose-5-phosphate reductoisomerase); the "ispD" gene (encoding a 2C-methyl-D-erythritol cytidyltransferase enzyme; also known as ygbP); the "ispE" gene (encoding 4-diphosphocytidyl-2-C-methylerythritol kinase; also known as ychB); the "ispF" gene (encoding a 2C-methyl-d-erythritol 2,4-cyclodiphosphate synthase; also known as ygbB); the "pyrG" gene (encoding a CTP synthase); the "lytB" gene involved in the formation of dimethylallyl diphosphate; the "gcpE" gene involved in the synthesis of 2-C-methyl-D-erythritol 4-phosphate; the "idi" gene (responsible for the intramolecular conversion of IPP to dimethylallyl pyrophosphate); and the "ispA" gene (encoding geranyltransferase or farnesyl diphosphate synthase) in the isoprenoid pathway.

The terms "lower carotenoid biosynthetic pathway", and "lower pathway" will be used interchangeably and refer to those enzymes which convert FPP to a suite of carotenoids. These include those genes and gene products that are involved in the immediate synthesis of either diapophytoene (whose synthesis represents the first step unique to biosynthesis of $C_{30}$ carotenoids) or phytoene (whose synthesis represents the first step unique to biosynthesis of $C_{40}$ carotenoids). All subsequent reactions leading to the production of various $C_{30}$–$C_{40}$ carotenoids are included within the lower carotenoid biosynthetic pathway. These genes and gene products comprise all of the "crt" genes including, but not limited to: crtM, crtN, crtN2, crtE, crtX, crtY, crtI, crtB, crtZ, and crtO. Finally, the term "carotenoid biosynthetic enzyme" is an inclusive term referring to any and all of the enzymes in the present pathway including, but not limited to: crtM, crtN, crtN2, crtE, crtX, crtY, crtI, crtB, crtZ, and crtO.

For the present application, the term "carotenoid compound" is defined as a class of hydrocarbons having a conjugated polyene carbon skeleton formally derived from isoprene, which is composed of triterpenes ($C_{30}$ diapocarotenoids) and tetraterpenes ($C_{40}$ carotenoids) and their oxygenated derivatives. These molecules typically have strong light absorbing properties and may range in length in excess of $C_{200}$. Other "carotenoid compounds" are known which are $C_{35}$, $C_{50}$, $C_{60}$, $C_{70}$, and $C_{80}$ in length, for example.

"Tetraterpenes" or "$C_{40}$ carotenoids" consist of eight isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{40}$ carotenoids may be formally derived from the acyclic $C_{40}H_{56}$ structure (Formula I below), having a long central chain of conjugated double bonds, by (i) hydrogenation, (ii) dehydrogenation, (iii) cyclization, (iv) oxidation, (v) esterification/glycosylation, or any combination of these processes. This class also includes certain compounds that arise from rearrangements of the carbon skeleton (I), or by the (formal) removal of part of this structure.

where the broken lines indicate formal division into isoprenoid units.

"Triterpenes" or "$C_{30}$ diapocarotenoids" consist of six isoprenoid units joined in such a manner that the arrangement of isoprenoid units is reversed at the center of the molecule so that the two central methyl groups are in a 1,6-positional relationship and the remaining nonterminal methyl groups are in a 1,5-positional relationship. All $C_{30}$ carotenoids may be formally derived from the acyclic $C_{30}H_{42}$ structure (Formula II below, hereinafter referred to as "diapophytoene" or "dehydrosqualene"), having a long central chain of conjugated double bonds, by (i) hydrogenation (ii) dehydrogenation, (iii) cyclization, (iv) oxidation, (v) esterification/glycosylation, or any combination of these processes.

Formula I

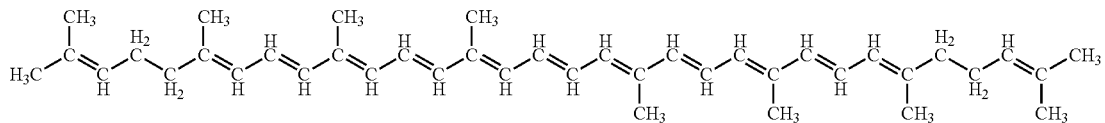

(I)

For convenience carotenoid formulae are often written in a shorthand form as (Formula IA below):

Formula IA

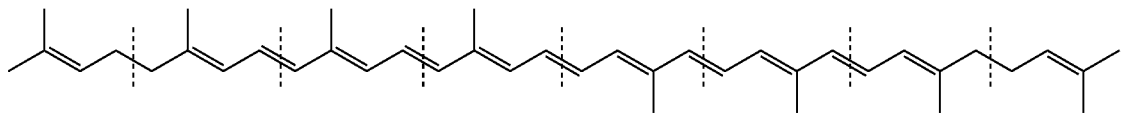

(IA)

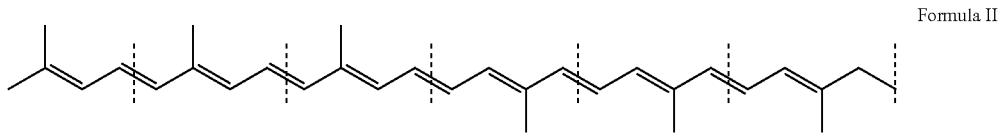

Formula II

The terms "diapolycopene" and "alapocarotene" are used interchangeably to refer to the fully unsaturated $C_{30}$ carotenoid backbone, which may be derived from diapophytoene via dehydrogenation.

The term "functionalized" or "functionalization" refers to the (i) hydrogenation, (ii) dehydrogenation, (iii) cyclization, (iv) oxidation, or (v) esterification/glycosylation of any portion of the carotenoid backbone. This backbone is defined as the long central chain of conjugated double bonds. Functionalization may also occur by any combination of the above processes. Specific functionalization discussed in the present application include: (1) creation of aldehydes (compounds containing RC(=O)H, in which a carbonyl group is bonded to one hydrogen atom and to one R group; and (2) creation of carboxylic acids (compounds containing the structure RC(=O)OH).

The term "omega-aldehyde functional group" or "omega-carboxyl functional group" refers to the creation of an aldehyde or carboxyl functional group, respectively, on the omega (i.e., end) carbon of the conjugated polyene carbon skeleton of the carotenoid compound.

The term "ψ group" will hereinafter refer to the end group of a carotenoid molecule possessing a $C_9H_{15}$ structure, as shown by the circled portion of the diaponeurosporene molecule in FIG. 2B. In contrast, a "desaturated ψ group" will refer to an end group, as represented by the formula $C_9H_{13}$ (shown as the boxed structure in FIG. 2A and 2B).

The terms "diapophytoene dehydrogenase" and "diapophytoene desaturase" are used interchangeably to refer to the CrtN enzyme whose native function is to introduce additional double bonds to the $C_{30}$ carotenoid precursor diapophytoene.

The term "CrtN" refers to the diapophytoene dehydrogenase enzyme encoded by the crtN gene represented in ORF 2 (Methylomonas 16a) and ORF 5 (Staphylococcus aureus) (see FIG. 3).

Figure 3A:
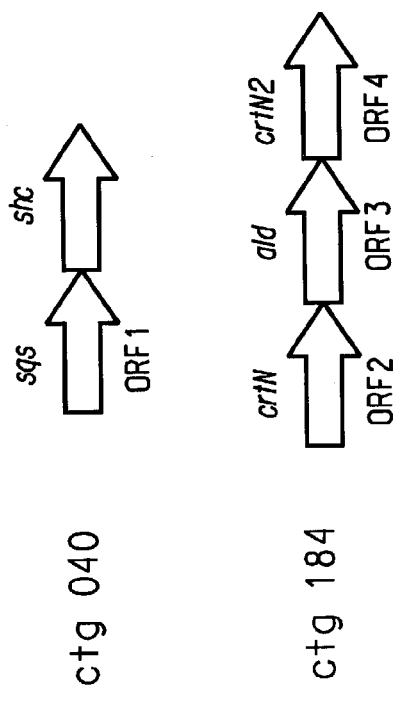
Figure 3B:
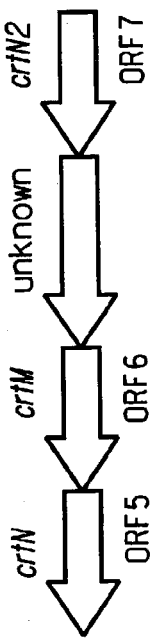
Figure 4A:
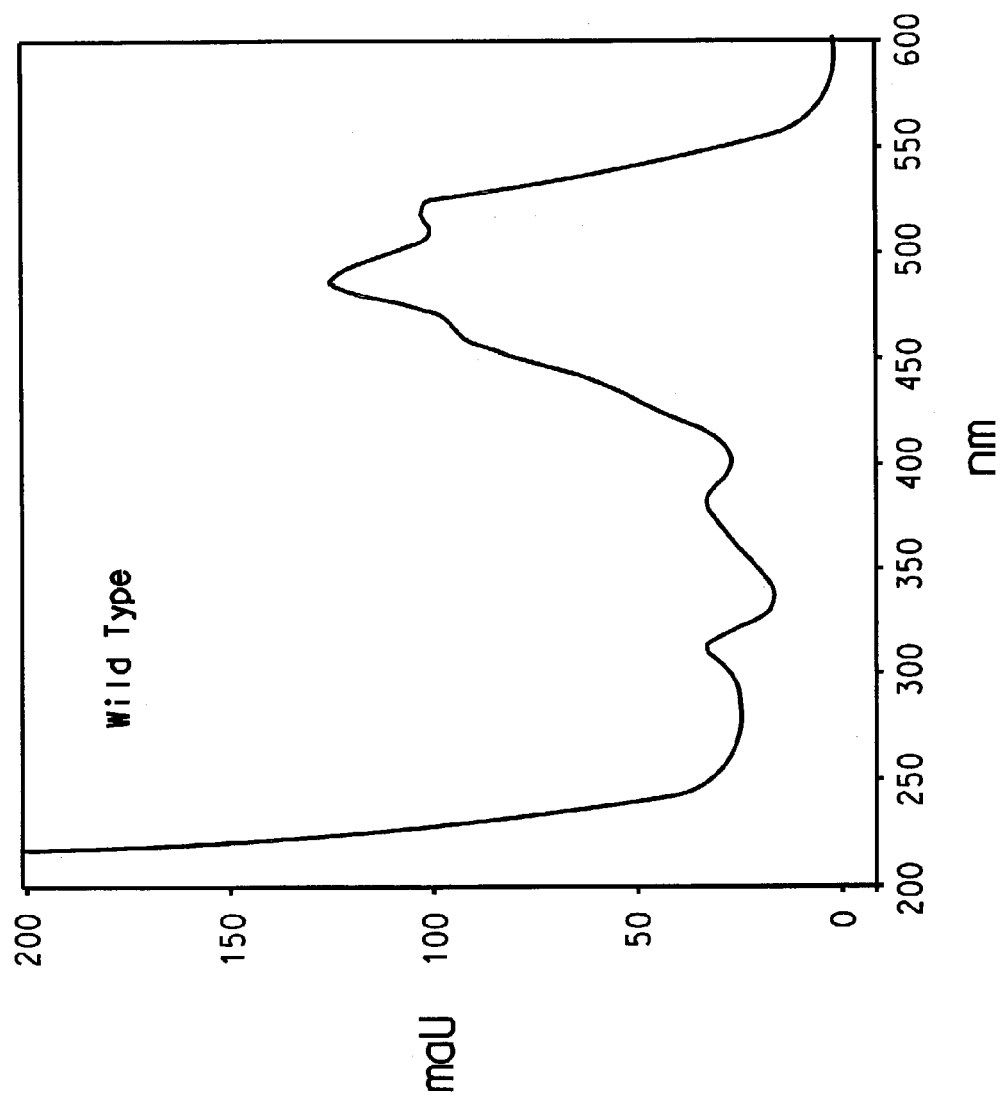
Figure 4B:
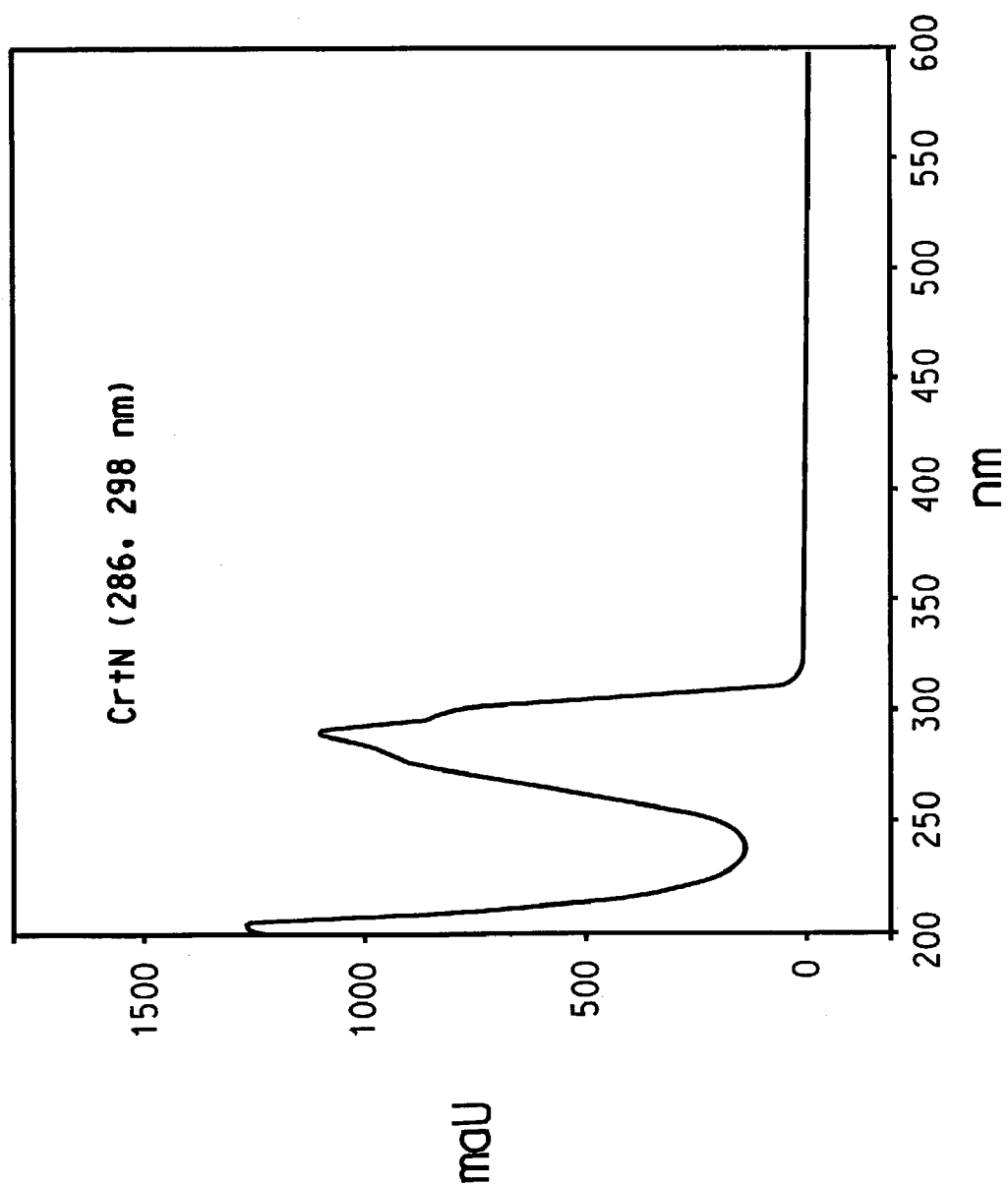
Figure 4C:
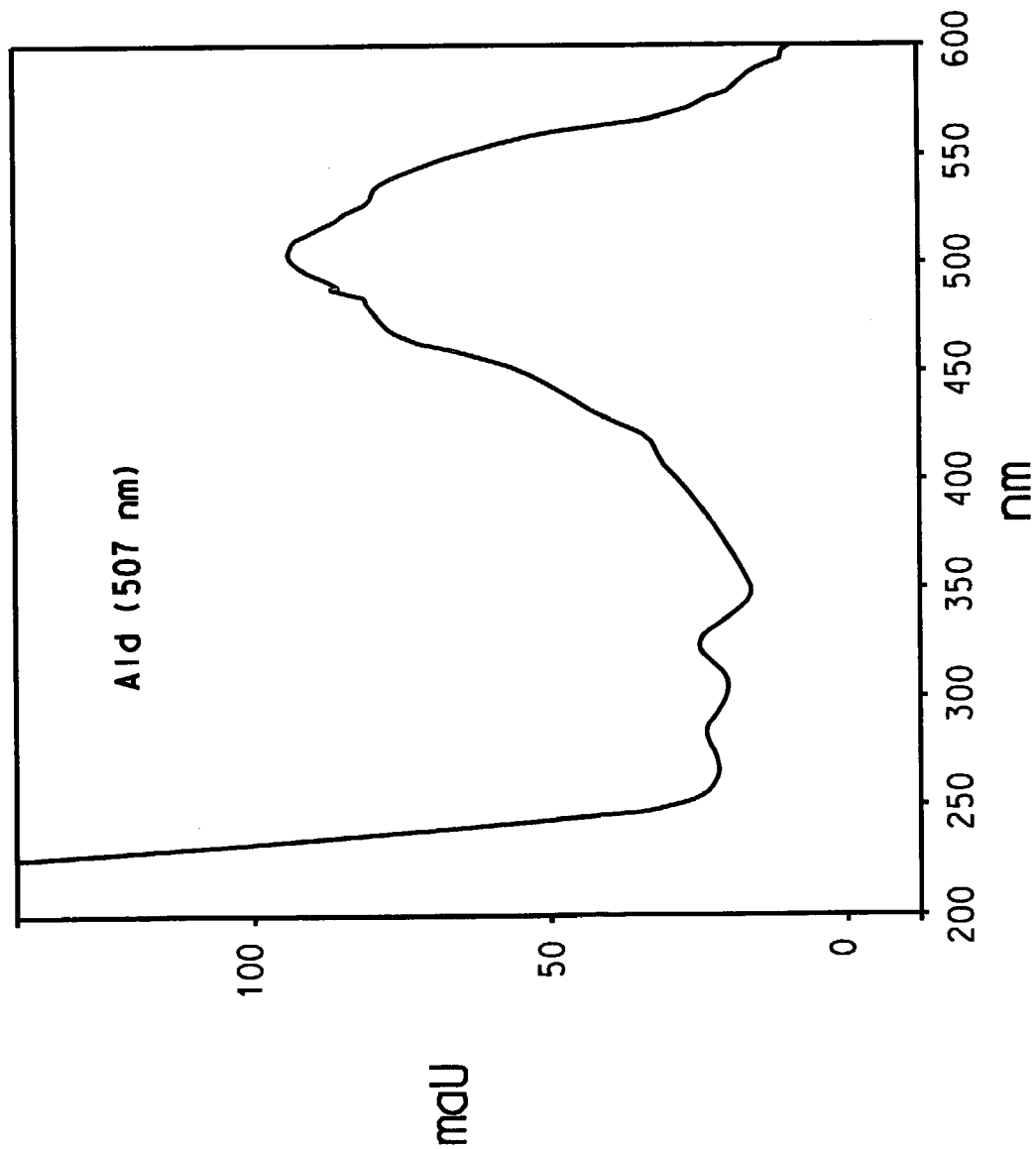
Figure 4D:
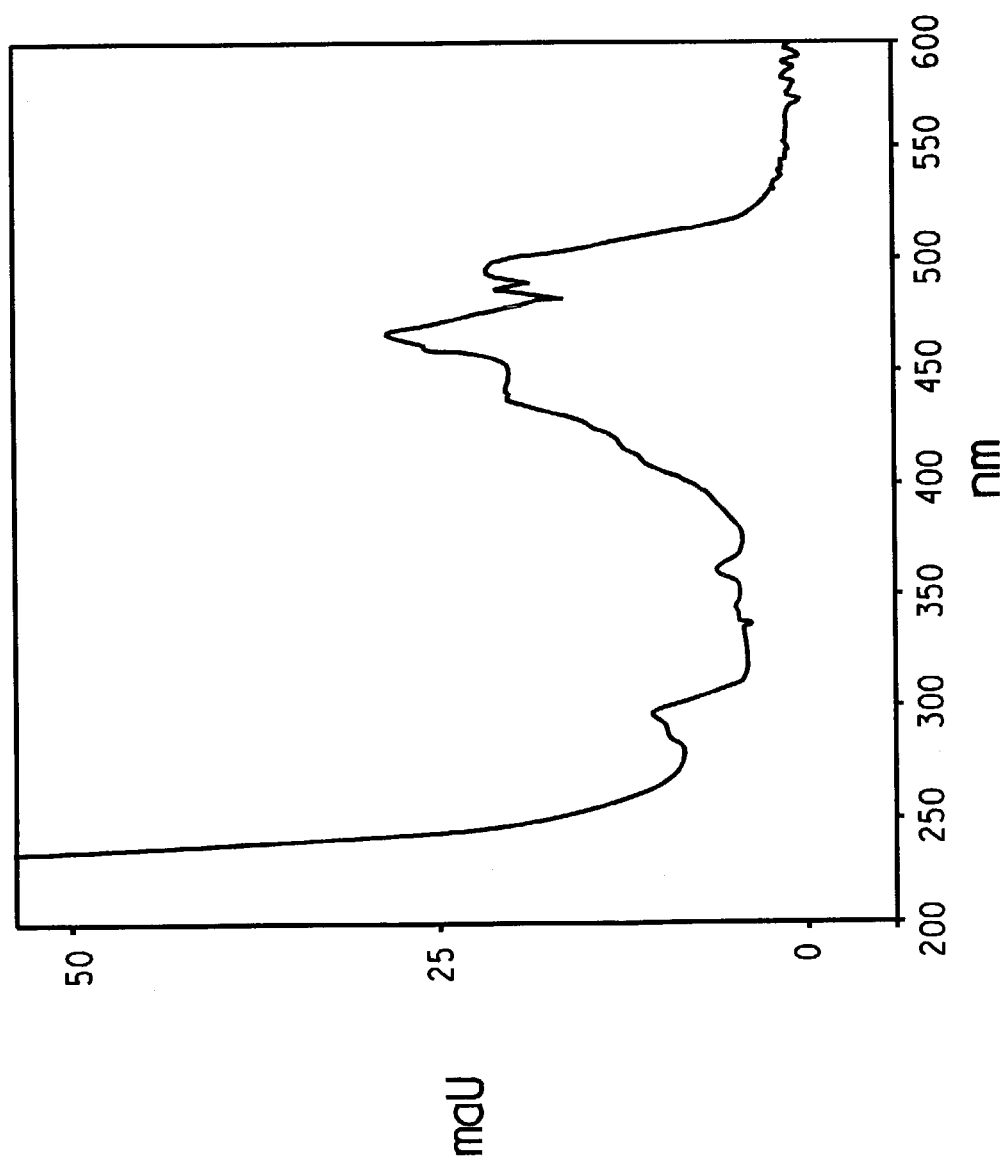

The term "CrtM" refers to the diapophytoene synthase enzyme encoded by the crtM gene represented in ORF 6 (see FIG. 3B).

The term "CrtN2" refers to the aldehyde introducing enzyme encoded by the crtN2 gene represented in ORF 4 (Methylomonas 16a) and ORF 7 (Staphylococcus aureus) (see FIG. 3).

The term "ald" refers to aldehyde dehydrogenase enzyme encoded by the ald gene represented in ORF 3 (see FIG. 3A).

The term "sqs" refers to the squalene dehydrogenase enzyme encoded by the sqs gene represented in ORF 1 (see FIG. 3A).

The term "Embden-Meyerhof pathway" refers to the series of biochemical reactions for conversion of hexoses such as glucose and fructose to important cellular 3-carbon intermediates such as glyceraldehyde 3-phosphate, dihydroxyacetone phosphate, phosphoenol pyruvate and pyruvate. These reactions typically proceed with net yield of biochemically useful energy in the form of ATP. The key enzymes unique to the Embden-Meyerof pathway are the phosphofructokinase and fructose 1,6 bisphosphate aldolase.

The term "Entner-Douderoff pathway" refers to a series of biochemical reactions for conversion of hexoses such as glucose or fructose to the important 3-carbon cellular intermediates pyruvate and glyceraldehyde 3-phosphate without any net production of biochemically useful energy. The key enzymes unique to the Entner-Douderoff pathway are the 6-phosphogluconate dehydratase and a ketodeoxyphosphogluconate aldolase.

The term "$C_1$ carbon substrate" or "single carbon substrate" refers to any carbon-containing molecule that lacks a carbon—carbon bond. Examples are methane, methanol, formaldehyde, formic acid, formate, methylated amines (e.g., mono-, di-, and tri-methyl amine), methylated thiols, and carbon dioxide.

The term "$C_1$ metabolizer" refers to a microorganism that has the ability to use a single carbon substrate as its sole source of energy and biomass. $C_1$ metabolizers will typically be methylotrophs and/or methanotrophs.

The term "methylotroph" means an organism capable of oxidizing organic compounds that do not contain carbon—carbon bonds. Where the methylotroph is able to oxidize $CH_4$, the methylotroph is also a methanotroph.

The term "methanotroph" or "methanotrophic bacteria" means a prokaryote capable of utilizing methane as its primary source of carbon and energy. Complete oxidation of methane to carbon dioxide occurs by aerobic degradation pathways. Typical examples of methanotrophs useful in the present invention include but are not limited to the genera *Methylomonas*, *Methylobacter*, *Methylococcus*, and *Methylosinus*.

The term "high growth methanotrophic bacterial strain" refers to a bacterium capable of growth with methane or methanol as the sole carbon and energy source and which possesses a functional Embden-Meyerof carbon flux pathway resulting in a high rate of growth and yield of cell mass per gram of $C_1$ substrate metabolized. The specific "high growth methanotrophic bacterial strain" described herein is referred to as "*Methylomonas* 16a", "16a" or "*Methylomonas* sp. 16a", which terms are used interchangeably and which refer to the *Methylomonas* strain used in the present invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60+ C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., ed.) Oxford University: NY (1988); 2.) *Biocomputing: Informatics and Genome Projects* (Smith, D. W., ed.) Academic: NY (1993); 3.) *Computer Analysis of Sequence Data, Part I* (Griffin, A. M., and Griffin, H. G., eds.) Humana: NJ (1994); 4.) *Sequence Analysis in Molecular Biology* (von Heinje, G., ed.) Academic (1987); and 5.) *Sequence Analysis Primer* (Gribskov, M. and Devereux, J., eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp *CABIOS.* 5:151–153 (1989)) with default parameters (GAP PENALTY=10, GAP LENGTH PENALTY=10). Default parameters for pairwise alignments using the Clustal method were: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, and preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs:1–14. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be—but are not limited to—intracellular localization signals.

The term "signal peptide" refers to an amino terminal polypeptide preceding the secreted mature protein. The signal peptide is cleaved from, and is therefore not present in, the mature protein. Signal peptides have the function of directing and translocating secreted proteins across cell membranes. A signal peptide is also referred to as a signal protein. "Transformation" refers to the transfer of a nucleic acid fragment into the genome of a host organism, resulting in genetically stable inheritance. Host organisms containing the transformed nucleic acid fragments are referred to as "transgenic", "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequences into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990); 3.) DNASTAR (DNASTAR, Inc. Madison, Wis.); and 4.) the FASTA program incorporating the Smith-Waterman algorithm (W. R. Pearson, *Comput. Methods Genome Res.,* [Proc. Int. Symp.] (1994), Meeting Date 1992, 111–20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual,* Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions,* Cold Spring Harbor Laboratory Cold Press Spring Harbor, N.Y. (1984); and by Ausubel, F. M. et al., *Current Protocols in Molecular Biology,* published by Greene Publishing Assoc. and Wiley-Interscience (1987).

Genes Involved in Carotenoid Production

The enzyme pathway involved in the biosynthesis of carotenoid compounds can be conveniently viewed in two parts, the upper isoprenoid pathway providing for the conversion of pyruvate and glyceraldehyde-3-phosphate to farnesyl pyrophosphate and the lower carotenoid biosynthetic pathway, which provides for the synthesis of either diapophytoene or phytoene and all subsequently produced carotenoids. The upper pathway is ubiquitous in many $C_1$ metabolizing microorganisms and in these cases it will only be necessary to introduce genes that comprise the lower pathway for the biosynthesis of the desired carotenoid. The division between the two pathways concerns the synthesis of farnesyl pyrophosphate (FPP). Where FPP is naturally present only elements of the lower carotenoid pathway will be needed. However, it will be appreciated that for the lower pathway carotenoid genes to be effective in the production of carotenoids, it will be necessary for the host cell to have suitable levels of FPP within the cell. Where FPP synthesis is not provided by the host cell, it will be necessary to introduce the genes necessary for the production of FPP. Each of these pathways will be discussed below in detail.

The Upper Isoprenoid Pathway

Isoprenoid biosynthesis occurs through either of two pathways, generating the common $C_5$ isoprene subunit, isopentenyl pyrophosphate (IPP). First, IPP may be synthesized through the well-known acetate/mevalonate pathway. However, recent studies have demonstrated that the mevalonate-dependent pathway does not operate in all living organisms. An alternate mevalonate-independent pathway for IPP biosynthesis has been characterized in bacteria and in green algae and higher plants (Horbach et al., *FEMS Microbiol. Lett.* 111:135–140 (1993); Rohmer et al, *Biochem.* 295: 517–524 (1993); Schwender et al., *Biochem.* 316: 73–80 (1996); Eisenreich et al., *Proc. Natl. Acad. Sci. USA* 93: 6431–6436 (1996)).

Many steps in the mevalonate-independent isoprenoid pathway are known (FIG. 1). For example, the initial steps of the alternate pathway leading to the production of IPP have been studied in *Mycobacterium tuberculosis* by Cole et al. (*Nature* 393:537–544 (1998)). The first step of the pathway involves the condensation of two 3-carbon molecules (pyruvate and D-glyceraldehyde 3-phosphate) to yield a 5-carbon compound known as D-1-deoxyxylulose-5-phosphate. This reaction occurs by the DXS enzyme, encoded by the dxs gene. Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR), encoded by the gene dxr. 2-C-methyl-D-erythritol-4-phosphate is subsequently converted into 4-diphosphocytidyl-2C-methyl-D-erythritol in a CTP-dependent reaction by the enzyme encoded by the non-annotated gene ygbP (Cole et al., supra). Recently, however, the ygbP gene was renamed as ispD as a part of the isp gene cluster (SwissProtein Accession #Q46893).

Next, the $2^{nd}$ position hydroxy group of 4-diphosphocytidyl-2C-methyl-D-erythritol can be phosphorylated in an ATP-dependent reaction by the enzyme encoded by the ychB gene. This product phosphorylates 4-diphosphocytidyl-2C-methyl-D-erythritol, resulting in 4-diphosphocytidyl-2C-methyl-D-erythritol 2-phosphate. The ychB gene was renamed as ispE, also as a part of the isp gene cluster (SwissProtein Accession #P24209). Finally, the product of the ygbB gene converts 4-diphosphocytidyl-2C-methyl-D-erythritol 2-phosphate to 2C-methyl-D-erythritol 2,4-cyclodiphosphate in a CTP-dependent manner. This gene has also been recently renamed, and belongs to the isp gene cluster. Specifically, the new name for the ygbB gene is ispF (SwissProtein Accession #P36663). The product of the pyrG gene is important in these reactions, as a CTP synthase.

The enzymes encoded by the IytB and gcpE genes (and perhaps others) are thought to participate in the reactions leading to formation of isopentenyl pyrophosphate (IPP) and dimethylallyl pyrophosphate (DMAPP). IPP may be isomerized to DMAPP via IPP isomerase, encoded by the idi gene; however, this enzyme is not essential for survival and may be absent in some bacteria using the 2-C-methyl-D-erythritol 4-phosphate (MEP) pathway. Recent evidence suggests that the MEP pathway branches before IPP and separately produces IPP and DMAPP via the lytB gene product. A IytB knockout mutation is lethal in E. coli except in media supplemented with both IPP and DMAPP.

The synthesis of FPP occurs via the isomerization of IPP to dimethylallyl pyrophosphate (DMAPP). This reaction is followed by a sequence of two prenyltransferase reactions catalyzed by ispA, leading to the creation of geranyl pyrophosphate (GPP; a 10-carbon molecule) and farnesyl pyrophosphate (FPP; a 15-carbon molecule).

The Lower Carotenoid Biosynthetic Pathway

The division between the upper isoprenoid pathway and the lower carotenoid pathway is somewhat subjective. Because FPP synthesis is common in both carotenogenic and non-carotenogenic bacteria, the Applicant considers the first step in the lower carotenoid biosynthetic pathway to begin with the conversion of farnesyl pyrophosphate (FPP) to compounds of two divergent pathways, which lead to the formation of either $C_{30}$ diapocarotenoids or $C_{40}$ carotenoids.

The $C_{40}$ Lower Carotenoid Biosynthetic Pathway

Within the $C_{40}$ pathway, the first step in the biosynthetic pathway begins with the prenyltransferase reaction converting farnesyl pyrophosphate (FPP) to geranylgeranyl pyrophosphate (GGPP). The gene crtE, encoding GGPP synthetase, is responsible for this prenyltransferase reaction, leading to the synthesis of phytoene. This reaction adds IPP to FPP to produce a 20-carbon molecule, geranylgeranyl pyrophosphate (GGPP).

Finally, a condensation reaction of two molecules of GGPP occurs to form phytoene (PPPP), the first 40-carbon molecule of the lower carotenoid biosynthesis pathway. This enzymatic reaction is catalyzed by crtB, encoding phytoene synthase.

From the compound phytoene, a spectrum of $C_{40}$ carotenoids are produced by subsequent hydrogenation, dehydrogenation, cyclization, oxidation, or any combination of these processes. For example, lycopene, which imparts a "red"-colored spectra, is produced from phytoene through four sequential dehydrogenation reactions by the removal of eight atoms of hydrogen, catalyzed by the gene crtI (encoding phytoene desaturase). Lycopene cyclase (crtY) converts lycopene to β-carotene. β-carotene is converted to zeaxanthin via a hydroxylation reaction resulting from the activity of β-carotene hydroxylase (encoded by the crtZ gene). β-carotene is converted to canthaxanthin by β-carotene ketolase encoded by the crtW gene. Canthaxanthin can then be converted to astaxanthin by β-carotene hydroxylase encoded by the crtZ gene. Zeaxanthin can be converted to zeaxanthin-β-diglucoside. This reaction is catalyzed by zeaxanthin glucosyl transferase (crtX). Zeaxanthin can be converted to astaxanthin by β-carotene ketolase encoded by crtW, crtO or bkt. These examples are not limiting and many other carotenoid genes and products exist within this $C_{40}$ lower carotenoid biosynthetic pathway.

The $C_{30}$ Lower Carotenoid Biosynthetic Pathway

Within the $C_{30}$ pathway, the first unique step in the biosynthetic pathway begins with the conversion of farnesyl pyrophosphate (FPP) to diapophytoene.

The pathway is well studied in Staphylcoccus aureus. The first committed reaction is the head-to-head condensation of two molecules of farnesyl diphosphate ($C_{15}$) by crtM, forming dehydrosqualene (Wieland, B. et al. J. Bacteriol. 176 (24): 7719–7726 (1994)). Subsequently, dehydrosqualene desaturase (crtN) is successively dehydrogenated in three steps to produce 4,4'-diaponeurosporene (Wieland et al., supra). However, at present time, public databases include only one single gene (Genbank Accession Number X73889) and 4 genomic sequences (NC002745, NC002758, AP003137, AP003365) of crtN and crtM, isolated from Staphylococcus aureus strains N315 and Mu50. A single report exists concerning the heterologous overexpression of crtN from S. aureus in E. coli (Raisig, A., and G. Sandmann. J. Bacteriol., 181(19):6184–6187 (1999)). Based on identification of carotenoid compounds, it is known that the next stages in the $C_{30}$ metabolic pathway for S. aureus involve introduction of oxygen functions on the terminal methyl group to produce aldehyde and carboxylic acid forms of the carotenoid (Marshall, J. H., and G. J. Wilmoth. J. Bacteriol. 147: 900–913 (1981) and 147: 914–919 (1981)). However, no genes have been identified that correspond to this function, until the present application.

In Methylomonas 16a, the crtN and crtN2 genes are known to participate in the conversion of farnesyl pyrophosphate to a naturally occurring 30-carbon pigment produced by the organism. Details of this reaction have not been understood until the present application.

Sequence Identification

A variety of nucleotide sequences have been isolated from Methylomonas 16a encoding gene products involved in the native $C_{30}$ lower carotenoid pathway. ORF's 1–4, for example, encode enzymes in the lower carotenoid biosynthetic pathway (see FIGS. 1 and 2A).

Comparison of the sqs nucleotide base and deduced amino acid sequences (ORF 1) to public databases reveals that the most similar known sequences range from about 60% identical to the amino acid sequence of sqs reported herein over a length of 363 amino acids using a Smith-Waterman alignment algorithm (W. R. Pearson, Comput. Methods Genome Res., [Proc. Int. Symp.] (1994), Meeting Date 1992, 111–20. Editor(s): Suhai, Sandor. Plenum: New York, N.Y.). More preferred amino acid fragments are at least about 70%–80% identical to the sequences herein, where about 80%–90% is preferred. Most preferred are nucleic acid fragments that are at least 95% identical to the amino acid fragments reported herein. Similarly, preferred sqs encoding nucleic acid sequences corresponding to the instant ORF's are those encoding active proteins and which are at least 80% identical to the nucleic acid sequences of reported herein. More preferred sqs nucleic acid fragments are at least 90% identical to the sequences herein. Most preferred are sqs nucleic acid fragments that are at least 95% identical to the nucleic acid fragments reported herein.

Comparison of the crtN nucleotide base and deduced amino acid sequences (ORF 2) to public databases reveals that the most similar known sequences range from about 34% identical to the amino acid sequence of crtN reported herein over a length of 511 amino acids using a Smith-Waterman alignment algorithm (W. R. Pearson, supra). More preferred amino acid fragments are at least about 70%–80% identical to the sequences herein, where about 80%–90% is preferred. Most preferred are nucleic acid fragments that are at least 95% identical to the amino acid fragments reported herein. Similarly, preferred crtN encoding nucleic acid sequences corresponding to the instant ORF's are those encoding active proteins and which are at least 80% identical to the nucleic acid sequences of reported herein. More preferred crtN nucleic acid fragments are at least 90% identical to the sequences herein. Most preferred are crtN nucleic acid fragments that are at least 95% identical to the nucleic acid fragments reported herein.

Comparison of the ald nucleotide base and deduced amino acid sequences (ORF 3) to public databases reveals that the most similar known sequences range from about 33% identical to the amino acid sequence of ald reported herein over a length of 530 amino acids using a Smith-Waterman alignment algorithm (W. R. Pearson, supra). More preferred amino acid fragments are at least about 70%–80% identical to the sequences herein, where about 80%–90% is preferred. Most preferred are nucleic acid fragments that are at least 95% identical to the amino acid fragments reported herein. Similarly, preferred ald encoding nucleic acid sequences corresponding to the instant ORF's are those encoding active proteins and which are at least 80% identical to the nucleic acid sequences of reported herein. More preferred ald nucleic acid fragments are at least 90% identical to the sequences herein. Most preferred are ald nucleic acid fragments that are at least 95% identical to the nucleic acid fragments reported herein.

Comparison of the crtN2 nucleotide base and deduced amino acid sequences (ORF 4) to public databases reveals that the most similar known sequences range from about 51% identical to the amino acid sequence of crtN2 reported herein over a length of 497 amino acids using a Smith-Waterman alignment algorithm (W. R. Pearson, supra). More preferred amino acid fragments are at least about 70%–80% identical to the sequences herein, where about 80%–90% is preferred. Most preferred are nucleic acid fragments that are at least 95% identical to the amino acid fragments reported herein. Similarly, preferred crtN2 encoding nucleic acid sequences corresponding to the instant ORF's are those encoding active proteins and which are at least 80% identical to the nucleic acid sequences of reported herein. More preferred crtN2 nucleic acid fragments are at least 90% identical to the sequences herein. Most preferred are crtN2 nucleic acid fragments that are at least 95% identical to the nucleic acid fragments reported herein.

Isolation of Homologs

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to: 1.) methods of nucleic acid hybridization; and 2.) methods of DNA and RNA amplification, as exemplified by various uses of nucleic acid amplification technologies (e.g. polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89: 392 (1992)).

For example, genes encoding similar proteins or polypeptides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach,* K. E. Davis Ed., (1986) pp 33–50 IRL: Herndon, Va.; and Rychlik, W., In *Methods in Molecular Biology,* White, B. A. (Ed.), (1993) Vol. 15, pp 31–39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Alternatively, the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers (e.g., sodium citrate, Tris-HCl, PIPES or HEPES (pH range about 6–9)), about 0.05 to 0.2% detergent (e.g., sodium dodecylsulfate), or between 0.5–20 mM EDTA, FICOLL (Pharmacia Inc.) (about 300–500 kdal), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate), and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1 (1984); Maniatis, supra).

Recombinant Expression—Microbial

The genes and gene products of the instant sequences may be produced in heterologous host cells, particularly in the cells of microbial hosts. Expression in recombinant microbial hosts may be useful for the expression of various carotenoid pathway intermediates, or for the modulation of carotenoid pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high level expression of the enzymes.

Accordingly, it is expected for example that introduction of chimeric genes encoding the instant bacterial enzymes under the control of the appropriate promoters will demonstrate increased production of functionalized carotenoids. It is contemplated that it will be useful to express the instant genes both in natural host cells as well as heterologous hosts. Introduction of the present genes into the native host will result in elevated levels of existing production of functionalized carotenoids. Additionally, the instant genes may also be introduced into non-native host bacteria where there are advantages to manipulate the carotenoid compound production that are not present the organisms from which the instant genes are directly isolated.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters which are useful to drive expression of the instant ORF's in the desired host cell are numerous and familiar to those skilled in the art. Virtually any promoter capable of driving these genes is suitable for the present invention including, but not limited to: CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary; however, it is most preferred if included.

Preferred Microbial Hosts

Preferred heterologous host cells for expression of the instant genes and nucleic acid fragments are microbial hosts that can be found broadly within the fungal or bacterial families and which grow over a wide range of temperature, pH values, and solvent tolerances. For example, it is contemplated that any bacteria, yeast, and filamentous fungi will be suitable hosts for expression of the present nucleic acid fragments. Because transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, and/or saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression.

Examples of host strains include, but are not limited to: fungal or yeast species such as *Aspergillus, Trichoderma, Saccharomyces, Pichia, Candida, Hansenula;* or bacterial species such as *Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Methylobacterium, Alcaligenes, Synechocystis, Synechococcus, Anabaena, Thiobacillus, Methanobacterium, Klebsiella, Myxococcus* and *Staphylococcus.*

Methylotrophs and *Methylomonas* sp. 16a as Microbial Hosts

The present invention provides for the expression of genes involved in the biosynthesis of carotenoid compounds in microorganisms that are able to use single carbon substrates as a sole energy source. Such microorganisms are referred to herein as C1 metabolizers. The host microorganism may be any C1 metabolizer that has the ability to synthesize farnesyl pyrophosphate (FPP) as the precursor for many of the carotenoids.

Many C1 metabolizing microorganisms are known in the art which are able to use a variety of single carbon substrates. Single carbon substrates useful in the present invention include, but are not limited to: methane, methanol, formaldehyde, formic acid, methylated amines (e.g. mono-, di- and tri-methyl amine), methylated thiols, and carbon dioxide.

All C1 metabolizing microorganisms are generally classified as methylotrophs. Methylotrophs may be defined as any organism capable of oxidizing organic compounds that do not contain carbon—carbon bonds. A subset of methylotrophs is the methanotrophs, which have the distinctive ability to oxidize methane. Facultative methylotrophs have the ability to oxidize organic compounds which do not contain carbon—carbon bonds, but may also use other carbon substrates such as sugars and complex carbohydrates for energy and biomass. Obligate methylotrophs are those organisms which are limited to the use of organic compounds that do not contain carbon—carbon bonds for the generation of energy and obligate methanotrophs are those obligate methylotrophs that have the ability to oxidize methane.

Facultative methylotrophic bacteria are found in many environments, but are isolated most commonly from soil, landfill and waste treatment sites. Many facultative methylotrophs are members of the β and γ subgroups of the Proteobacteria (Hanson et al., *Microb. Growth C1 Compounds.,* [Int. Symp.], 7$^{th}$ (1993), pp 285–302. Editor(s): Murrell, J. Collin and Don P. Kelly. Intercept: Andover, UK; Madigan et al., *Brock Biology of Microorganisms,* 8$^{th}$ ed., Prentice Hall: UpperSaddle River, N.J. (1997)). Facultative methylotrophic bacteria suitable in the present invention include, but are not limited to: *Methylophilus, Methylobacillus, Methylobacterium, Hyphomicrobium, Xanthobacter, Bacillus, Paracoccus, Nocardia, Arthrobacter, Rhodopseudomonas,* and *Pseudomonas.*

The ability to utilize single carbon substrates is not limited to bacteria but extends also to yeasts and fungi. A number of yeast genera are able to use single carbon substrates as energy sources in addition to more complex-materials. Specific methylotrophic yeasts useful in the present invention include, but are not limited to: *Candida, Hansenula, Pichia, Torulopsis,* and *Rhodotorula.*

Those methylotrophs having the additional ability to utilize methane are referred to as methanotrophs. Of particular interest in the present invention are those obligate methanotrophs which are methane utilizers but which are obliged to use organic compounds lacking carbon—carbon bonds. Exemplary of these organisms are included in, but not limited to, the genera *Methylomonas, Methylobacter, Methylococcus, Methylosinus, Methylocyctis, Methylomicrobium,* and *Methanomonas.*

Of particular interest in the present invention are high growth obligate methanotrophs having an energetically favorable carbon flux pathway. For example, Applicants have discovered a specific strain of methanotroph having several pathway features that makes it particularly useful for carbon flux manipulation. This type of strain served as the host organism from which ORFs 1–4 were isolated and is known as *Methylomonas* 16a (ATCC PTA 2402). It is obvious to one skilled in the art that this particular strain and other related methylotrophs are preferred microbial hosts for expression of the gene products of this invention, useful for the production of functionalized carotenoids.

The present strain contains several anomalies in the carbon utilization pathway. For example, based on genome sequence data, the strain is shown to contain genes for two pathways of hexose metabolism. The Entner-Douderoff Pathway (which utilizes the keto-deoxy phosphogluconate aldolase enzyme) is present in the strain. It is generally well accepted that this is the operative pathway in obligate methanotrophs. Also present, however, is the Embden-Meyerhof Pathway (which utilizes the fructose bisphosphate aldolase enzyme). It is well known that this pathway is either not present, or not operative, in obligate methanotrophs. Energetically, the latter pathway is most favorable and allows greater yield of biologically useful energy, ultimately resulting in greater yield production of cell mass and other cell mass-dependent products in *Methylomonas* 16a. The activity of this pathway in the present 16a strain has been confirmed through microarray data and biochemical evidence measuring the reduction of ATP. Although the 16a strain has been shown to possess both the Embden-Meyerhof and the Entner-Douderoff pathway enzymes, the data suggests that the Embden-Meyerhof pathway enzymes are more strongly expressed than the Entner-Douderoff pathway enzymes. This result is surprising and counter to existing beliefs concerning the glycolytic metabolism of methanotrophic bacteria. Applicants have discovered other methanotrophic bacteria having this characteristic, including for example, *Methylomonas clara* and *Methylosinus sporium*. It is likely that this activity has remained undiscovered in methanotrophs due to the lack of activity of the enzyme with ATP, the typical phosphoryl donor for the enzyme in most bacterial systems.

A particularly novel and useful feature of the Embden-Meyerhof pathway in strain 16a is that the key phosphofructokinase step is pyrophosphate-dependent instead of ATP-dependent. This feature adds to the energy yield of the pathway by using pyrophosphate instead of ATP. Because of its significance in providing an energetic advantage to the strain, this gene in the carbon flux pathway is considered diagnostic for the present strain.

In methanotrophic bacteria, methane is converted to biomolecules via a cyclic set of reactions known as the ribulose monophosphate pathway or RuMP cycle. This pathway is comprised of three phases, each phase being a series of enzymatic steps. The first step is "fixation" or incorporation of C-1 (formaldehyde) into a pentose to form a hexose or six-carbon sugar. This occurs via a condensation reaction between a 5-carbon sugar (pentose) and formaldehyde and is catalyzed by hexulose monophosphate synthase. The second phase is termed "cleavage" and results in splitting of that hexose into two 3-carbon molecules. One of those 3-carbon molecules is recycled back through the RuMP pathway and the other 3-carbon fragment is utilized for cell growth.

In methanotrophs and methylotrophs the RuMP pathway may occur as one of three variants. However only two of these variants are commonly found: the FBP/TA (fructose bisphosphotase/transaldolase) or the KDPG/TA (keto deoxy phosphogluconate/transaldolase) pathway (Dijkhuizen L., G. E. Devries. "The Physiology and biochemistry of aerobic methanol-utilizing gram negative and gram positive bacteria". In: *Methane and Methanol Utilizers;* Colin Murrell and Howard Dalton, Eds.; Plenum: NY, 1992).

The present strain is unique in the way it handles the "cleavage" steps where genes were found that carry out this conversion via fructose bisphosphate as a key intermediate. The genes for fructose bisphosphate aldolase and transaldolase were found clustered together on one piece of DNA. Secondly, the genes for the other variant involving the keto deoxy phosphogluconate intermediate were also found clustered together. Available literature teaches that these organisms (obligate methylotrophs and methanotrophs) rely solely on the KDPG pathway and that the FBP-dependent fixation pathway is utilized by facultative methylotrophs (Dijkhuizen et al., supra). Therefore the latter observation is expected, whereas the former is not. The finding of the FBP genes in an obligate methane-utilizing bacterium is both surprising and suggestive of utility. The FBP pathway is energetically favorable to the host microorganism due to the fact that more energy (ATP) is utilized than is utilized in the KDPG pathway. Thus, organisms that utilize the FBP pathway may have an energetic advantage and growth advantage over those that utilize the KDPG pathway. This advantage may also be useful for energy-requiring production pathways in the strain. By using this pathway, a methane-utilizing bacterium may have an advantage over other methane-utilizing organisms as production platforms for either single cell protein or for any other product derived from the flow of carbon through the RuMP pathway.

Accordingly, the present invention provides a method for the production of a functionalized carotenoid compound in a high growth, energetically favorable *Methylomonas* strain which (a) grows on a C1 carbon substrate selected from the group consisting of methane and methanol; and (b) comprises a functional Embden-Meyerhof carbon pathway, said pathway comprising a gene encoding a pyrophosphate-dependent phosphofructokinase enzyme.

In Vitro Bio-Conversion of Carotenoids

Alternatively, it is possible to carry out the bioconversions of the present application in vitro. Where substrates for the crtN2, ald and sqs enzymes are not synthesized endogenously by the host cell it will be possible to add the substrate exogenously. In this embodiment the suitable carotenoid substrate may be solubilized with mild detergent (e.g., DMSO) or mixed with phospholipid vesicles. To assist in transport into the cell the host cell may optionally be permeabilized with a suitable solvent such as toluene. Methods for this type of in-vitro bio-conversion of carotenoid substrates has basis in the art (see for example: Hundle, B. S., et al., *FEBS*, 315:329–334 (1993); and Bramley, P. M., et al. *Phytochemistry*, 26:1935–1939 (1987)).

Pathway Engineering

Knowledge of the sequence of the present genes will be useful in manipulating the carotenoid biosynthetic pathways in any organism having such a pathway and particularly in methanotrophs. Methods of manipulating genetic pathways are common and well known in the art. Selected genes in a particular pathway may be up-regulated or down-regulated by variety of methods. Additionally, competing pathways in an organism may be eliminated or sublimated by gene disruption and similar techniques.

Once a key genetic pathway has been identified and sequenced, specific genes may be up-regulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, U.S. Pat. No. 5,565,350; Zarling et al., PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods for gene down regulation is targeted gene disruption where foreign DNA is inserted into a structural gene so as to disrupt transcription. This can be effected by the creation of genetic cassettes comprising the DNA to be inserted (often a genetic marker) flanked by sequences having a high degree of homology to a portion of the gene to be disrupted. Introduction of the cassette into the host cell results in insertion of the foreign DNA into the structural gene via the native DNA replication mechanisms of the cell. (See for example Hamilton et al. *J. Bacteriol.* 171:4617–4622 (1989); Balbas et al. *Gene* 136:211–213 (1993); Gueldener et al. *Nucleic Acids Res.* 24:2519–2524 (1996); and Smith et al. *Methods Mol. Cell. Biol.* 5:270–277(1996).)

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See, for example: Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36: 227 (1992).

Another non-specific method of gene disruption is the use of transposable elements or transposons. Transposons are genetic elements that insert randomly in DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass., based upon the bacterial transposon Tn7; and the EZ::TN Transposon Insertion Systems, available from Epicentre Technologies, Madison, Wis., based upon the Tn5 bacterial transposable element).

Within the context of the present invention, it may be useful to modulate the expression of the identified carotenoid pathway by any one of the methods described above. For example, the present invention provides several genes encoding key enzymes in the lower carotenoid pathway leading to the production of functionalized carotenoid compounds. The isolated genes include the crtN, ald, and crtN2 genes. In particular it may be useful to up-regulate the initial condensation of 3-carbon compounds (pyruvate and C1 aldehyde group, D-glyceraldehyde 3-phosphate), to yield the 5-carbon compound D-1-deoxyxylulose-5-phosphate mediated by the dxs gene. Alternatively, if it is desirable to produce a specific functionalized $C_{30}$ carotenoid compound, it may be desirable to: 1.) over-express the sqs or crtM genes and crtN, ald, and crtN2; and 2.) knockout the crtE genes leading to the synthesis of $C_{40}$ carotenoids.

Industrial Production

Where commercial production of the instant carotenoid compounds are desired a variety of culture methodologies may be applied. For example, large-scale production of a specific gene product overexpressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase, where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in: Thomas D. Brock in *Biotechnology: A Textbook of Industrial Microbiology*, 2nd ed., (1989) Sinauer Associates: Sunderland, Mass.; or Deshpande, Mukund V., *Appl. Biochem. Biotechnol.*, 36:227 (1992), each herein incorporated by reference.

Commercial production of the instant carotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products, or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include, but are not limited to: monosaccharides (e.g., glucose and fructose), oligosaccharides (e.g., lactose or sucrose), polysaccharides (e.g., starch or cellulose or mixtures thereof, and unpurified mixtures from renewable feedstocks (e.g., cheese whey permeate, cornsteep liquor, sugar beet molasses, and barley malt). Additionally the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon-containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1Compd.*, [Int. Symp.], 7th (1993), pp 415–32. Murrell, J. Collin and Don P. Kelly, Eds. Intercept: Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

Recombinant Expression—Plants

Plants and algae are also known to produce carotenoid compounds. The nucleic acid fragments of the instant invention may be used to create transgenic plants having the ability to express the microbial genes for the production of functionalized carotenoids. Preferred plant hosts will be any variety that will support a high production level of the instant carotenoids. Suitable green plants will include, but are not limited to: soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum sp*), barley (*Hordeum vulgare*), oats (*Avena sativa*, L), sorghum (*Sorghum bicolor*), rice (*Oryza sativa*), *Arabidopsis*, cruciferous vegetables (e.g., broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but are not limited to commercially significant hosts such as *Spirulina, Haemotacoccus*, and *Dunalliela*. Overexpression of the carotenoid compounds may be accomplished by first constructing chimeric genes of the present invention in which the coding regions are operably linked to promoters capable of directing expression of a gene in the desired plant tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences of the present invention should be capable of promoting expression of the present gene product. High-level plant promoters that may be used in this invention, for example, include the promoter of the small subunit (ss) of the ribulose-1,5-bisphosphate carboxylase from soybean (Berry-Lowe et al., *J. Molecular and App. Gen.*, 1:483–498 1982)), and the promoter of the chlorophyll a/b binding protein. These two promoters are known to be light-induced in plant cells (see, for example, *Genetic Engineering of Plants, an Agricultural Perspective*, A. Cashmore, Plenum: NY (1983), pp 29–38; Coruzzi, G. et al., *J. Biol. Chem.*, 258:1399 (1983); and Dunsmuir, P. et al., *J. Mol. Appl. Genetics*, 2:285 (1983)).

Plasmid vectors comprising the instant chimeric genes can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus multiple events must be screened in order to obtain lines displaying the desired expression level and pattern. Such screening may be accomplished by Southern analysis of DNA blots (Southern, *J. Mol. Biol.* 98:503 (1975)), Northern analysis of mRNA expression (Kroczek, J. Chromatogr Biomed. Appl., 618(1–2):133–145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.* 100: 1627–1632 (1992)) added and/or with targeting sequences that are already present removed. While the references cited give examples of each of these, the list is not exhaustive and more targeting signals of utility may be discovered in the future that are useful in the invention.

Protein Engineering

It is contemplated that the present nucleotides may be used to produce gene products having enhanced or altered activity. Various methods are known for mutating a native gene sequence to produce a gene product with altered or enhanced activity including, but not limited to: 1.) error prone PCR (Melnikov et al., i Nucleic Acids Research, 27(4): 1056–1062 (Feb. 15, 1999)); 2.) site directed mutagenesis (Coombs et al., *Proteins* (1998), pp 259–311, 1 plate. Angeletti, Ruth Hogue, Ed., Academic: San Diego, Calif.); and 3.) "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double-stranded and can be of various lengths ranging from 50 bp to 10 kb. The sequences may be randomly digested into fragments ranging from about 10 bp to 1000 bp, using restriction endonucleases well known in the art (Maniatis, supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably the temperature is from about 80° C. to 100° C. The nucleic acid fragments may be reannealed by cooling. Preferably the temperature is from about 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from about 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocols (Manatis, supra).

Furthermore, a hybrid protein can be assembled by fusion of functional domains using the gene shuffling (exon shuffling) method (Nixon et al., *PNAS*, 94:1069–1073 (1997)). The functional domain of the instant gene can be combined with the functional domain of other genes to create novel enzymes with desired catalytic function. A hybrid enzyme may be constructed using PCR overlap extension methods and cloned into various expression vectors using the techniques well known to those skilled in art.

Enzyme Functionality

Figure 2A:
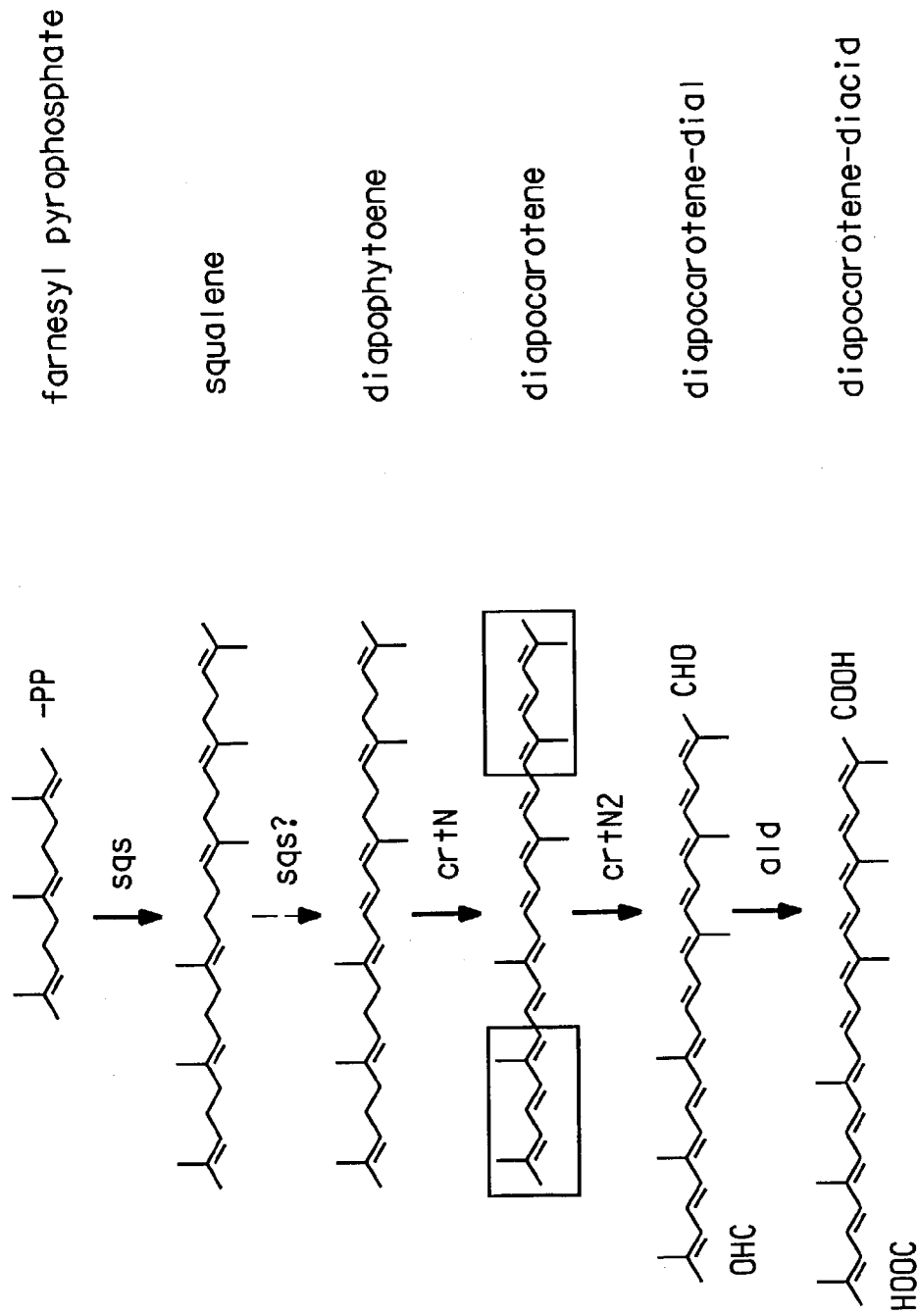
Figure 2B:
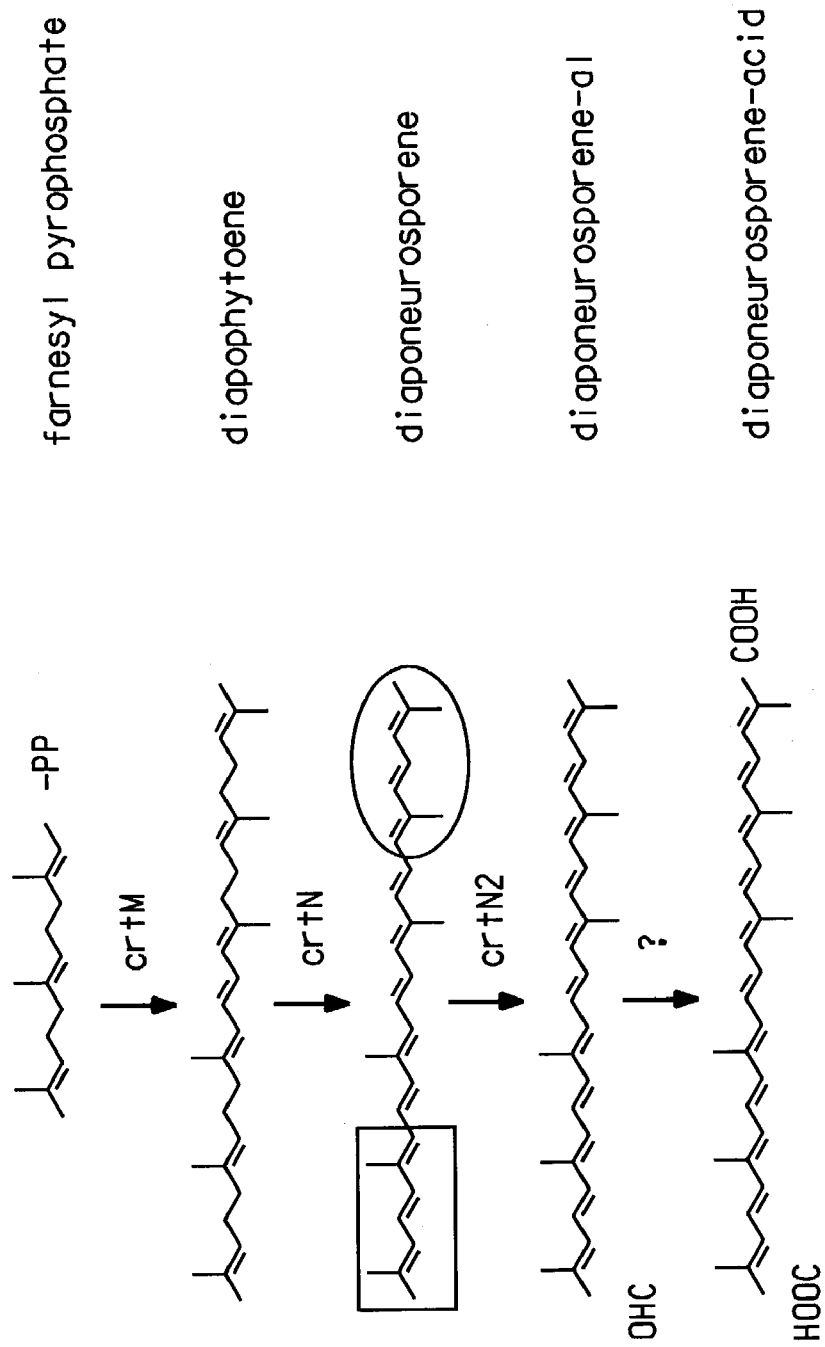
FIG. 2B shows proposed pathways for $C_{30}$ carotenoid biosynthesis in *Staphylococcus aureus*.

The pathway for $C_{30}$ carboxy-carotenoid synthesis in *Methylomonas* 16a and *Staphylococcus aureus* can be compared in FIGS. 2A and B. Both pathways require farnesyl pyrophophate as a precursor molecule; however, different genes are responsible for the formation of diapophytoene. In *Methylomonas*, the condensation of farnesyl pyrophophate is catalyzed by the sqs gene, to yield squalene. Squalene is then converted to diapophytoene by an unknown mechanism. This biosynthetic process whereby squalene acts as a key intermediate corresponds with that proposed by Kleinig, H. and R. Schmitt for *Pseudomonas rhodos* (*Z. Naturforsch* 37c: 758–760 (1982)). In contrast, the present studies confirmed that farneysl pyrophosphate is directly converted to diapophytoene in *S. aureus*, a reaction catalyzed by the well known crtM gene encoding dehydrosqualene synthase (Wieland, et al, *J. Bacteriol.* 176:7719–7726 (1994)).

The common substrate diapophytoene is then successively desaturated by a diapophytoene desaturase (crtN) to form either diapocarotene in *Methylomonas* 16a, or 4,4'-diaponeurosporene in *S. aureus*. The subsequent reaction on each of these substrates appears to be catalyzed by the crtN2 genes. Of particular importance in the present invention, crtN2 genes have been identified in both *Methylomonas* 16a and *S. aureus* that possess great homology to one another (51% identity and 68% homology, based on comparison of the *S. aureus* gene to that of 16a). Previous to this study, the crtN2 gene of *S. aureus* was identified as a hypothetical protein. Following the gene's identication based on homology to the crtN2 of *Methylomonas*, the gene was amplified from *S. aureus* (ATCC 35556) and subsequently functionally characterized.

Although the crtN2 gene acts on different substrates, careful analysis of its function reveals that both crtN2 genes possess the ability to produce omega-aldehyde functional groups on those carotenoid compounds which possess a 7-8 or 7'-8' desaturated $\psi$ group. Thus, it has been shown that diapocarotene is converted to diapocarotene-dial in 16a, while in *S. aureus* the crtN2 enzyme is responsible for the conversion of diaponeurosporene to diaponeurosporene-al. Evidence for the interchangeability of these genes, due to their common functionality, is provided in studies which demonstrated that the *Methylomonas* crtN2 and *Staphylococcus* crtN2 genes both catalyze the synthesis of diaponeurosporene-al from diaponeurosporene in *E. coli* (Example 8). Thus, it is hypothesized that the functionalization produced by the activity of the crtN2 genes, whereby an omega-aldehyde functional group(s) is added to a carotenogenic substrate, should be readily extendable to a variety of carotenoid compounds, any of which possess the following general formula of:

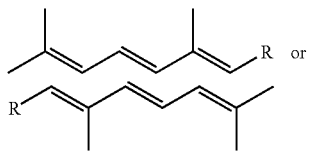

wherein R represents the remaining length of the conjugated polyene carbon skeleton (or carotenogenic backbone). Useful carotenoids of the present invention may have a length in excess of $C_{200}$ where a length of about $C_{30}$ to about $C_{80}$ is preferred. This critical end group is highlighted in FIGS. 2A and B (see boxes drawn on the end groups of diapocarotene and diapophytoene). In addition to diapocarotene and diaponeurosporene, other suitable substrates would also include, but are not limited to: 3,4-didehydrolycopene, 3,4,3',4'-tetradehydrolycopene, torulene, 4-ketotorulene, celaxanthin (3-hydroxytorulene), 3-hydroxy-4-ketotorulene, 1-hydroxy-3,4,3',4'-tetradehydro-1,2-dihydro-I, I-carotene, 3,4-didehydrochlorobactene, 8'-apo-β-carotene, and 8'-apo-β-caroten-3-ol.

Following the formation of diapocarotene-dial in the *Methylomonas* 16a $C_{30}$ biosynthetic pathway, Applicants have identified an aldehyde dehydrogenase gene (ald) which catalyzes the oxidation of the diapocarotene-dial aldehyde to its corresponding carboxylic acid (diapocarotene-diacid) (FIG. 2A). Functional analysis of the gene reveals that it possesses the ability to form an omega-carboxyl functional group on the 7-8 and 7'-8' desaturated ψ group, containing the omega carbon, of the conjugated polyene carbon skeleton of the carotenoid substrate. It is contemplated that this enzymes's substrates would include any substrate having the general formula OHC—R or R—CHO wherein R is the remaining length of the conjugated polyene carbon skeleton. Specific preferred substrates will include, but are not limited to: diapocarotene-dial, diaponeurosporene-al, 3,4-didehydrolycopene-al, 3,4,3',4'-tetradehydrolycopene-dial, torulene-al, 4-ketotorulene-al, celaxanthin-al (3-hydroxytorulene-al), 3-hydroxy-4-ketotorulene-al, 1-hydroxy-3,4,3',4'-tetradehydro-1,2-dihydro-I, I-carotene-al, 3,4-didehydrochlorobactene-al, 8'-apo-β-caroten-8'-al, apo-2-zeaxanthinal, and apo-8'-lycopenal. Although a similar chemical reaction occurs in the *S. aureus* $C_{30}$ pathway, whereby carboxylation of diaponeurosporene-al occurs to produce diaponeurosporene-acid, the gene catalyzing this particular reaction has not yet been identifed.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: Sambrook, J., Fritsch, E. F. and Maniatis, T. *Molecular Cloning: A Laboratory Manual;* Cold Spring Harbor Laboratory: Cold Spring Harbor, N.Y. (1989) (Maniatis); by T. J. Silhavy, M. L. Bennan, and L. W. Enquist, Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience (1987).

Materials and methods suitable for the maintenance and growth of bacterial cultures are well known in the art. Techniques suitable for use in the following examples may be found as set out in: *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or, by Thomas D. Brock in *Biotechnology: A Textbook of Industrial Microbiology,* 2nd ed., Sinauer Associates: Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. In any case where GCG program parameters were not prompted for, in these or any other GCG program, default values were used.

The meaning of abbreviations is as follows: "sec" means second(s), "min" means minute(s), "h" means hour(s), "d" means day(s), "μL" means microliter(s), "mL" means milliliter(s), "L" means liter(s), "μM" means micromolar, "mM" means millimolar, "M" means molar, "mmol" means millimole(s), "μmole" mean micromole(s)", "g" means gram(s), "μg" means microgram(s), "ng" means nanogram(s), "U" means unit(s), "bp" means base pair(s), and "kB" means kilobase(s).

Plasmids

For ease of understanding, the following plasmids were used in these studies (Table 2).

TABLE 2

Plamids used in this application

| Plasmid | Backbone | Expressed genes and Organism* |
|---------|----------|-------------------------------|
| PDCQ150 | pCR2.1   | cdN1 (16a)-ald (16a)-crtN2 (16a) |
| PDCQ151 | pBHR1    | crtN1 (16a)-ald (16a)-crtN2 (16a) |
| PDCQ153 | pTrcHis2 | crtM (*S. aureus*) |
| PDCQ154 | pTrcHis2 | sqs (16a) |
| PDCQ155 | pTrcHis2 | crtM (*S. aureus*)-crtNl (16a)-ald (16a)-crtN2 (16a) |
| PDCQ158 | pTrcHis2 | crtN2 (*S. aureus*) |
| PDCQ159 | PTrcHis2 | crtM (*S. aureus*)-crtNl (16a)-ald (16a) |
| PDCQ160 | PTrcHis2 | crtM (*S. aureus*)-crtNl (16a)-ald (16a)-crtN2 (*S. aureus*) |
| pDCQ165 | pTrcHis2 | crtM (*S. aureus*)-crtN (*S. aureus*) |
| pDCQ166 | pBHR1    | crtM (*S. aureus*)-crtN (*S. aureus*) |
| pDCQ167 | pTrcHis2 | crtN2 (16a) |
| pDCQ168 | pTrcHis2 | crtN2 (*S. aureus*) |

*Organism refers to that from which the gene was isolated.

Microbial Cultivation and Associated Analyses for *Methylomonas* 16a

The following conditions were used throughout the experimental Examples for treatment of *Methylomonas* 16a, unless alternative conditions were specifically mentioned.

*Methylomonas* 16a is typically grown in serum stoppered Wheaton bottles (Wheaton Scientific, Wheaton Ill.) using a gas/liquid ratio of at least 8:1 (i.e., 20 mL of Nitrate liquid "BTZ-3" media in 160 mL total volume). The standard gas phase for cultivation contained 25% methane in air. These conditions comprise growth conditions and the cells are referred to as growing cells. In all cases, the cultures were grown at 30° C. with constant shaking in a Lab-Line rotary shaker unless otherwise specified.

Nitrate Medium for *Methylomonas* 16a

Nitrate liquid medium, also referred to herein as "defined medium" or "BTZ-3" medium was comprised of various salts mixed with Solution 1 as indicated below (Tables 3 and 4); or, where specified, the nitrate was replaced with 15 mM ammonium chloride. Solution 1 provides the composition for a 100 fold concentrated stock solution of trace minerals.

TABLE 3

Solution 1*

|  | MW | Conc. (mM) | g per L |
| --- | --- | --- | --- |
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.7 | 0.77 | 0.184 |

*Mix the gram amounts designated above in 900 mL of $H_2O$, adjust to pH = 7, and add $H_2O$ to an end volume of 1 L. Keep refrigerated.

TABLE 4

Nitrate liquid medium (BTZ-3)**

|  | MW | Conc. (mM) | g per L |
| --- | --- | --- | --- |
| $NaNO_3$ | 84.99 | 10 | 0.85 |
| $KH_2PO_4$ | 136.09 | 3.67 | 0.5 |
| $Na_2SO_4$ | 142.04 | 3.52 | 0.5 |
| $MgCl_2 \times 6H_2O$ | 203.3 | 0.98 | 0.2 |
| $CaCl_2 \times 2H_2O$ | 147.02 | 0.68 | 0.1 |
| 1 M HEPES (pH 7) | 238.3 |  | 50 mL |
| Solution 1 |  |  | 10 mL |

**Dissolve in 900 mL $H_2O$. Adjust to pH = 7, and add $H_2O$ to give 1 L. For agar plates: Add 15 g of agarosein 1 L of medium, autoclave, let cool down to 50° C., mix, and pour plates.

Carotenoid Determination for *Methylomonas* 16a

For carotenoid determination, *Methylomonas* 16a was grown in 100 mL BTZ medium under methane (25%) for three days to stationary phase. Cells were spun down, washed with distilled water, and freeze-dried (lyophilizer: Virtis, Gardiner, N.Y.) for 24 h in order to determine dry-weights. After the dry-weight of each culture was determined, cells were extracted.

First, cells were welled with 0.4 mL of water and let stand for 15 min. After 15 min, 4 mL of acetone was added and thoroughly vortexed to homogenize the sample. The samples were then shaken at 30° C. for 1 hr. After 1 hr, the cells were centrifuged. Pink coloration was observed in the supernatant. The supernatant was collected and pellets were extracted again with 0.3 mL of water and 3 mL of acetone. The supernatants from the second extraction were lighter pink in color. The supernatants of both extractions were combined. Their volumes were measured and analyzed spectrophotometrically.

A crude acetone extract from *Methylomonas* 16a cells has a typical absorption spectrum (460 nm, 491 nm, 522 nm) measured by spectrophotometer (Amersham Pharmacia Biotech, Piscataway, N.J.).

HPLC Analysis of Carotenoid Content

A Beckman System Gold® HPLC with Beckman Gold Nouveau Software (Columbia, Md.) was used for the study. HPLC conditions were as follows: 125×4 mm RP8 (5 μm particles) column with corresponding guard column (Hewlett-Packard, San Fernando, Calif.); flow rate: 1 mL/min; solvent program: 0–10 min linear gradient from 15% water/85% methanol to 100% methanol, then 100% methanol for 10–20 min. The spectral data was collected by a Beckman photodiode array detector (model 168).

Example 1

Isolation of *Methylomonas* 16a

The original environmental sample containing the isolate was obtained from pond sediment. The pond sediment was inoculated directly into defined medium with ammonium as the nitrogen source under 25% methane in air. Methane was the sole source of carbon and energy. Growth was followed until the optical density at 660 nm was stable, whereupon the culture was transferred to fresh medium such that a 1:100 dilution was achieved. After 3 successive transfers with methane as the sole carbon and energy source, the culture was plated onto BTZ-3 agar with ammonium as nitrogen source and incubated under 25% methane in air. Many methanotrophic bacterial species were isolated in this manner. However, *Methylomonas* 16a was selected as the organism to study due to its rapid growth of colonies, large colony size, ability to grow on minimal media, and pink pigmentation indicative of an active biosynthetic pathway for carotenoids.

Example 2

Native Carotenoid of *Methylomonas* 16a

HPLC analysis of acetone extracts of the native carotenoids produced by *Methylomonas* 16a confirmed that one major carotenoid (net retention volume at about 6 mL) is responsible for the pink coloration of the wild-type and transconjugant *Methylomonas* 16a cells.

In order to confirm the structure of this major carotenoid, *Methylobacterium rhodinum* (formerly *Pseudomonas rhodos:* ATCC 14821) of which $C_{30}$-carotenoid was identified was used as a reference strain (Kleinig et al., *Z. Naturforsch* 34c, 181–185 (1979); Kleinig and Schmitt, *Z. Naturforsch* 37c, 758–760 (1982)). A saponified extract of *Methylobacterium rhodinum* and of *Methylomonas* 16a were compared by HPLC analysis under the same conditions as described in the General Methods. The results are shown as follows:

Saponified *M. rhodinum:*
  Absorption maxima: 460 nm, 487 nm, 517 nm
  Net retention volume=1.9 mL Saponified *Methylomonas* 16a:
    Absorption maxima: 460 nm, 488 nm, 518 nm
    Net retention volume=2.0 mL
    HPLC analysis results suggested that the carotenoid from *Methylomonas* 16a has the same $C_{30}$ carotenoic acid backbone as that from *Methylobacterium rhodinum*. Chemical reduction experiments were also performed to verify the carboxylation of the 16a carotenoid. The carotenoid carboxylic acids or their esters can only be reduced by $LiAlH_4$ to their primary corresponding carotenols. The carbonyl function of carotenoid aldehyde or ketone can be reduced by $NaBH_4$ or $LiAlH_4$ to alcohol.
    Experiments showed that the 16a native carotenoid was reduced by $LiAlH_4$ as indicated by color change from pink to yellow as well as the HPLC analysis. However, it could not be reduced by $NaBH_4$. The results were consistent with the presence of the carboxylic acid or ester group in the native 16a carotenoid.

Example 3

Genomic Sequencing of *Methylomonas* 16a

Genomic DNA was isolated from *Methylomonas* 16a according to standard protocols. Genomic DNA and library construction were prepared according to published protocols (Fraser et al., *Science* 270 (5235):397–403 (1995)). A cell pellet was resuspended in a solution containing 100 mM Na-EDTA pH 8.0, 10 mM Tris-HCl pH 8.0, 400 mM NaCl, and 50 mM $MgCl_2$.

Genomic DNA preparation After resuspension, the cells were gently lysed in 10% SDS, and incubated for 30 min at 55° C. After incubation at room temperature, proteinase K was added to 100 μg/mL and incubated at 37° C. until the suspension was clear. DNA was extracted twice with Tris-equilibrated phenol and twice with chloroform. DNA was precipitated in 70% ethanol and resuspended in a solution containing 10 mM Tris-HCl and 1 mM Na-EDTA (TE), pH 7.5. The DNA solution was treated with a mix of RNAases, then extracted twice with Tris-equilibrated phenol and twice with chloroform. This was followed by precipitation in ethanol and resuspension in TE.

Library construction 200 to 500 μg of chromosomal DNA was resuspended in a solution of 300 mM sodium acetate, 10 mM Tris-HCl, 1 mM Na-EDTA, and 30% glycerol, and sheared at 12 psi for 60 sec in an Aeromist Downdraft Nebulizer chamber (IBI Medical Products, Chicago, Ill.). The DNA was precipitated, resuspended and treated with Bal31 nuclease. After size fractionation, a fraction (2.0 kb or 5.0 kb) was excised and cleaned, and a two-step ligation procedure was used to produce a high titer library with greater than 99% single inserts.

Sequencing A shotgun sequencing strategy approach was adopted for the sequencing of the whole microbial genome (Fleischmann, R. et al., *Science* 269(5223):496–512 (1995)). Sequence was generated on an ABI Automatic sequencer using dye terminator technology (U.S. Pat. No. 5,366,860; EP 272,007) using a combination of vector and insert-specific primers. Sequence editing was performed in either DNAStar (DNA Star Inc.) or the Wisconsin GCG program (Wisconsin Package Version 9.0, Genetics Computer Group (GCG), Madison, Wis.) and the CONSED package (version 7.0). All sequences represent coverage at least two times in both directions.

Example 4

Identification and Characterization of Bacterial Genes from *Methylomonas*

All sequences from Example 3 were identified by conducting BLAST (Basic Local Alignment Search Tool; Altschul, S. F., et al., *J. Mol. Biol.* 215:403–410 (1993), searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The sequences were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. All comparisons were done using either the BLASTNnr or BLASTXnr algorithm.

The results of these BLAST comparisons are given below in Table 5 for genes of the present invention. Table 5 summarizes the sequence to which each *Methylomonas* gene has the most similarity (presented as % similarities, % identities, and Expectation values). The table displays data based on the BLASTXnr algorithm with values reported in Expect values. The Expect value estimates the statistical significance of the match, specifying the number of matches, with a given score, that are expected in a search of a database of this size absolutely by chance.

Two carotenoid biosynthesis gene clusters were identified in the genomic sequence of *Methylomonas* sp. 16a, as shown in FIG. 3A. The first gene cluster was identifed containing 2 genes (FIG. 3A). The gene sqs (ORF 1) encodes a putative squalene synthase with the highest BLAST hit to squalene synthase from *Methylococcus capsulatus* (60% identity and 73% similarity). The second gene was identifed as a squalene-hopene cyclase (shc) gene. Shc catalyzes the complex cyclization of squalene to the pentacyclic triterpene skeleton of hopanoids, a pathway that is not related to the lower carotenoid pathway.

In a second operon, three genes were encoded on this cluster. The first gene (designated crtN; ORF 2) encodes a putative diapophytoene dehydrogenase with the highest BLAST hit to a diapophytoene dehydrogenase from *Heliobacillus mobilis* (34% identity and 58% similarity). The middle gene (designated ald; ORF 3) encodes a putative aldehyde dehydrogenase with the highest BLAST hit to a betaine aldehyde dehydrogenase from *Arabidopsis thaliana* (33% identity and 50% similarity). The third gene (designated crtN2; ORF 4) also encodes a putative diapophytoene dehydrogenase with the highest BLAST hit to a hypothetical protein of phytoene dehydrogenase family from *Staphylococcus aureus* (51% identity and 67% similarity).

TABLE 5

| ORF Name | Gene Name | Similarity Identified | SEQ ID | SEQ ID peptide | % Identity[a] | % Similarity[b] | E-value[c] | Citation |
|---|---|---|---|---|---|---|---|---|
| 1 | sqs | emb|CAA71097.1 squalene synthase [Methylococcus capsulatus] | 1 | 2 | 60 | 73 | e-109 | Tippelt, A. etal., Biochim. Biophys. Acta 1391: 223–232 (1998) |
| 2 | crtN | pir|T31463|CrtN diapophytoene dehydrogenase [Heliobacillus mobiis] | 3 | 4 | 34 | 58 | e-93 | Xiong, J. et al., PNAS. 95 (6685):14851–14856 (1998) |
| 3 | ald | gb|AAG50992.1|AC036 106_5 betaine aldehyde dehydrogenase [Arabidopsis thaliana] | 5 | 6 | 33 | 50 | 4e-66 | Lin, X. et al., Unpublished |
| 4 | crtN2 | dbj|BAB43655.1| hypothetical protein ORF SA2351 Staphylococcus aureus] | 7 | 8 | 51 | 67 | e-133 | Kuroda, M. et al., Lancet 397 (9264):1225–1240 (1998) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.
% Identity, % similarity, and e-values are all reported according to FASTA analysis with Smith-Waterman computation.

Example 5

Synthesis of $C_{30}$ Carboxy-Carotenoids in Recombinant *E. coli*

Function of the *Methylomonas* 16a carotenoid gene cluster was tested in *E. coli* strains engineered to produce the $C_{30}$ carotenoid precursor. *E. coli* is naturally able to synthesize farnesyl pyrophosphate (FPP) using the upstream isoprenoid pathway.

Two *E. coli* strains were constructed by either expressing:
1.) the crtM gene from *Staphylococcus aureus* strain NCTC8325 (ATCC 35556) (FIG. 3B). The staphylococcal crtM gene was shown to encode a dehydrosqualene synthase (Wieland, et al. *J. Bacteriol.* 176:7719–7726 (1994)), although no crtM homolog was identified in the *Methylomonas* 16a genome; or
2.) the sqs gene from *Methylomonas* 16a on the pTrcHis2 expression vector (Table 2). The sqs of *Methylomonas* was located on a contig adjacent to a squalene-hopene cyclase (shc) (FIG. 3A). Squalene synthases from *Arabidopsis thaliana* and other sources were shown to be able to form dehydrosqualene as a secondary product in addition to squalene (Nakashima, T., et al., *PNAS*, 92:2328–2332 (1995)).

Primers crtM_F/Staphyl (SEQ ID NO:15) and crtM_R/Staphyl (SEQ ID NO:16) was used to amplify the 869 bp crtM gene from *Staphylococcus aureus* ATCC 35556. Primers sqs_F/16a (SEQ ID NO:17) and sqs_R/16a (SEQ ID NO:18) were used to amplify the 1098 bp sqs gene from *Methylomonas* 16a. The amplified gene products were cloned into the pTrcHis2 expression vector (Invitrogene, Carlsbad, Calif.) and the constructs with crtM or sqs genes in forward orientation were designated as pDCQ153 or pDCQ154, respectively (Table 2).

Primers crtN_FL (SEQ ID NO:19) and crtN_RL (SEQ ID NO:20) were used to amplify the 4668 bp crtN ald crtN2 gene cluster from *Methylomonas* 16a. The amplified product was first cloned into pCR2.1-TOPO vector (Invitrogen). The BsaI fragment of the TOPO construct (pDCQ150) containing the crtN ald crtN2 cluster was then cloned into the EcoRI site of the pBHR1 vector (MobiTec, Marco Island, Fla.). The pBHR1 construct containing the cluster in forward orientation with respect to the $Cm^r$ gene promoter was designated pDCQ151 (Table 2).

*E. coli* MG1655 strains co-transformed with pDCQ153/pDCQ151 or pDCQ154/pDCQ151 were pink, indicating active expression of the carotenoid synthesis genes. HPLC analysis of the pink transformants showed the presence of the carotenoid with the same absorption spectra (465 nm, 489–491 nm, 518–520 nm) as the 16a native carotenoid, suggesting that $C_{30}$ carboxy-carotenoid was produced in both recombinant *E. coli* strains. The retention time of the carotenoid from *E. coli* (11.0–11.7, average 11.4 min) was different from that of the 16a native carotenoid (12.7 min). This most likely resulted from the lack of ester formation in *E. coli*. LC-MS analysis confirmed that the molecular weight of the carboxy-carotenoid produced in E. coli was 460 daltons.

These results indicated that both staphylococcal crtM and *Methylomonas* sqs genes were expressed and were able to produce a $C_{30}$ carotenoid precursor in *E. coli*. Further, the *Methylomonas* crtN ald crtN2 genes were sufficient to convert the $C_{30}$ precursor to produce the carboxy-carotenoid in *E. coli*.

Example 6

Functional Determination of the *Methylomonas* crt Genes in $C_{30}$ Carotenoid Synthesis by Transposon Mutagenesis Transposon mutagenesis was performed to determine the function of each gene involved in the $C_{30}$ carboxy-caro tenoid synthesis and to identify the molecular mechanism for carboxylation function. To facilitate the mutagenesis, the four required crt genes for producing carboxy-carotenoid in *E. coli* were strung together by subcloning the 4.7 kb Bsa I fragment of pDCQ150 containing the three *Methylomonas* crtN ald crtN2 genes into the EcoRI site downstream of the staphylococcal crtM gene in pDCQ153. The resulting construct pDCQ155 contained the crtM gene and the crtN ald crtN2 genes in the same orientation, under the control of the trc promoter from the pTrcHis2 vector (Table 2). HPLC analysis showed that *E. coli* MG1655 transformed with pDCQ155 produced the same pink carboxy-carotenoid as the strain transformed with both pDCQ153 and pDCQ151 constructs.

In vitro transposon mutagenesis was performed on PDCQ155 DNA, using the EZ::TN™<TET-1>Insertion Kit (Epicentre, Madison, Wis.). The transposon-treated pDCQ155 DNA was transformed into TOP10 competent cells (Invitrogen). Cells containing transposon insertions were selected on LB plates with 10 μg/mL tetracycline. The white color clones were PCR screened for transposon insertion into the crtM or crtN genes, using primers TET-1 RP from the kit and crtM_F/Staphyl (SEQ ID NO:15). The orange, pink or red color clones were PCR screened for transposon insertion into the ald or crtN2 genes, using primers TET-1 FP from the kit and crtN_R (SEQ ID NO:21).

Positive clones were further sequenced to map the insertion site within respective genes. TOP10 cells carrying the wild type pDCQ155 or transposon mutations were cultured in 200 mL LB medium with 100 μg/mL ampicillin or 10 μg/mL tetracycline at 30° C. for 2 days. Cells were pelleted by centrifigation at 4000 g for 15 min. Carotenoids were extracted from the cell pellets with 10 mL methanol followed by 10 mL acetone, then dried under nitrogen and redissolved in 1 mL of methanol. Each sample of 100 μl was loaded onto HPLC for analysis as described in the General Methods.

Table 6 summarizes the HPLC analysis of the carotenoids in the transposon mutants, while FIG. 4 (A, B, C, and D) shows absorption spectra of the $C_{30}$ carotenoids in *E. coli* containing the wild type *Methylomonas* crtN gene cluster or the cluster with transposon insertions. Mutant w32 with a transposon insertion in the crtM gene did not produce any carotenoid, which confirmed the known function of the *Staphylococcus aureus* crtM responsible for synthesis of the $C_{30}$ carotenoid precursor diapophytoene.

TABLE 6

Summary of the phenotypes of the pDCQ155: Tn5 mutants

| Strain | Color | Transposon Insertion site (bp) | Mutated gene | Elution time (min) | Absorption Spectrum (nm) | Carotenoid |
|---|---|---|---|---|---|---|
| Wild type PDCQ155 | Pink | N/A* | N/A* | 11.4 | 465, 489–491, 518–520 | 4,4'-diapo-carotene 4,4' diacid |
| w32 | white | 869 | crtM (422–1285) | ND* | ND* | ND* |
| w13 | white | 1748 | crtN (1318–2853) | 15.1 | 286, 298 | 4,4'-diapo phytoene |
| p33 | deep red | 3764 | ald (2856–4448) | 12.4 | 507 | 4,4'-diapo-carotene dial |

TABLE 6-continued

Summary of the phenotypes of the pDCQ155: Tn5 mutants

| Strain | Color | Transposon Insertion site (bp) | Mutated gene | Elution time (min) | Absorption Spectrum (nm) | Carotenoid |
|---|---|---|---|---|---|---|
| | | | | 15.1 | 286, 298 | 4,4'-diapo phytoene |
| w18 | light orange | 5817 | crtN2 (4448–5941) | 14.2 | 442, 468, 498 | 4,4'-diapo carotene |
| | | | | 14.8 | 329, 346, 366 | 4,4'-diapophy-tofluene |
| | | | | 15.1 | 286, 298 | 4,4'-diapo-phytoene |

*N/A: not applicable.
*ND: no carotenoid detected.

Mutant w13 with a transposon insertion in the crtN gene produced only the colorless $C_{30}$ carotenoid precursor diapophytoene. This is consistent with the function of the *Methylomonas* crtN to encode a diapophytoene dehydrogenase as suggested by BLAST analysis. Mutant p33 with a transposon insertion in the ald gene produced the 4,4'-diapocarotene dialdehyde in addition to the diapophytoene precursor. This also confirmed the function of the *Methylomonas* ald to encode an aldehyde dehydrogenase as suggested by BLAST analysis.

Mutant w18 with a transposon insertion in the crtN2 gene produced the fully unsaturated $C_{30}$ carotenoid backbone 4,4'-diapocarotene in addition to some less unsaturated intermediates. Although crtN2 appeared to be a protein of the phytoene dehydrogenase family from the COG analysis (Tatusov, R. L. et al., Science 278(5338):631–7 (Oct. 24, 1997); Nucleic Acids Res. 29(1):22–8 (2001)), its homology with crtN was rather low (28% identity, 52% similarity). Analysis of the w18 mutant also indicated that crtN2 was not a diapophytoene dehydrogenase gene. The fact that only the $C_{30}$ carotenoid backbones were produced in the w18 mutant suggested that the omega-end group functionalization was blocked in this mutant. CrtN2 likely encodes an enzyme that introduces the aldehyde groups to the end of the 4,4'-diapocarotene to produce 4,4'-diapocarotene dialdehyde ("diapocarotene-dial"), which is further oxidized by the aldehyde dehydrogenase to produce the $C_{30}$-carboxy carotenoid 4,4'-diapocarotene diacid (FIG. 2A).

Example 7

Identification of the *Staphylococcus aureus* crt Genes for Carboxylating $C_{30}$ Carotenoids

*Staphylococcus aureus* is another group of bacteria that have been reported to synthesize $C_{30}$ carboxy-carotenoids (Marshall, J. H., et al., *J. Bacteriol.* 147:914–919 (1981); Taylor, R. F., et al., *J. Biochem. Cell Biol.* 61:892–905 (1983)). The pathway for $C_{30}$-carboxy-carotenoid synthesis in *S. aureus* was proposed as shown in FIG. 2B. Two genes [crtM (SEQ ID NO:9; ORF 6) and crtN (SEQ ID NO:11; ORF 5)] have been characterized to be involved in the $C_{30}$ carotenoid backbone synthesis (Wieland, B. et al, *J. Bacteriol.* 176:7719–7726 (1994)). However, the molecular mechanism for carboxylation of carotenoids in *S. aureus* has not been identified.

To determine if *S. aureus* employs a similar carboxylation mechanism as *Methylomonas* 16a for carotenoid synthesis, the CrtN2 from *Methylomonas* 16a was used to search the *S. aureus* genome databases. The CrtN2 homologs were identified in the six finished or unfinished genomes of *S. aureus* strains. They are over 99% identical among the different *S. aureus* strains and highly homologous to *Methylomonas* 16a CrtN2 (51% identity and 68% similarity). The CrtN2 homologs in the two finished genomes of *S. aureus* strain N315 (ORF ID: SA2351) and strain Mu50 (ORF ID: SAV2564) were both annotated as hypothetical proteins. The CrtN2 homolog in the genome of *S. aureus* strain NCTC 8325 was at position 410887–409394 and was not annotated. Since genomic DNA from *S. aureus* strain NCTC 8325 is available from ATCC (ATCC 35556D), primers were designed to amplify the homolog of the crtN2 gene using the genomic DNA from *S. aureus* NCTC 8325 as the template. The 1519 bp crtN2 homolog (SEQ ID NO:13; amino acid sequence presented as SEQ ID NO:14; ORF 7) was amplified by primers crtN2_F/Staphyl (SEQ ID NO:22) and crtN2_R/NCTC8325 (SEQ ID NO:23) and cloned into the pTrcHis2 vector, resulting in creation of pDCQ158 (Table 2).

To determine if the Staphylococcal crtN2 homolog performs the same function as the *Methylomonas* crtN2, the *Methylomonas* crtN2 on pDCQ155 was replaced by the staphylococcal crtN2 homolog (Table 2).

Specifically, the *Methylomonas* crtN2 was deleted from pDCQ155 by digesting with SnaBI and BsaBI, and the 1.5 kb EcoRI fragment from pDCQ158 containing the staphylococcal crtN2 homolog was blunt-ended with the Klenow enzyme and ligated to the large SnaBI-BsaBI fragment of pDCQ155. In the resulting construct pDCQ160, the staphylococcal crtN2 homolog was co-transcribed with the staphylococcal crtM and the *Methylomonas* crtN and ald genes. The self-ligated large SnaBI-BsaBI fragment of pDCQ155 (designated pDCQ159) contained only the staphylococcal crtM, *Methylomonas* crtN and ald genes without any crtN2.

The *E. coli* transformants of pDCQ160 were pink, compared to the light orange color of the pDCQ159 transformants. This indicated that the staphylococcal crtN2 homolog on pDCQ160 was actively expressed and contributed to the color difference of the transformants. HPLC analysis of the carotenoids showed that a carotenoid corresponding to diapocarotene-diacid (465 nm, 491 nm, 520 nm) was present in pDCQ160 transformants, whereas only the non-functionalized carotenoid backbone diapocarotene (442 nm, 465 nm, 495 nm) was present in pDCQ159 transformants (Table 7).

TABLE 7

Summary of the CrtN2 activity from *Staphylococcus aureus* and *Methylomonas*

| plasmid | Substrate | Functionalization genes | Elution time (min) | HPLC Spectra (nm) | Carotenoids identified |
|---|---|---|---|---|---|
| PDCQ 159 | diapolycopene | None | 14.2 | 442, 466, 498 | 4,4'-diapolycopene |
| PDCQ 155 | diapolycopene | crtN2 (16a) + ald (16a) | 11.4 | 464, 490, 520 | 4,4'-diapocarotene-4,4' acid |
| PDCQ 160 | diapolycopene | crtN2 (staph) + ald (16a) | 11.4 | 464, 490, 520 | 4,4'-diapocarotene-4,4' acid |

The fact that the same carboxy-carotenoid was observed with pDCQ 160 and PDCQ 155 suggested that the staphylococcal CrtN2 homolog performed the same function as the *Methylomonas* CrtN2 to introduce two aldehyde groups to the diapocarotene backbone, which were further oxidized to carboxylic acid groups by the *Methylomonas* ald (FIG. 2A).

Example 8

Functionalization of diaponeurosporene by CrtN2 From *Staphylococcus aureus* and *Methylomonas* 16a There are at least two noticeable differences between the $C_{30}$ carboxy-carotenoids synthesized by *Staphylococcus aureus* and those synthesized by *Methylomonas* 16a. The $C_{30}$ carotenoid in *Staphylococcus* has a carboxy group only on one end of the diaponeurosporene backbone. The $C_{30}$ carotenoid in *Methylomonas* has carboxy groups on both ends of the diapocarotene backbone. In the previous example, the staphylococcal crtN2 was shown to be able to add aldehyde groups to both ends of diapocarotene, which was further oxidized by the aldehyde dehydrogenase to produce diapocarotene-diacid. This suggested that the one end carboxylated carotenoid in *Staphylococcus* was not due to the asymmetric activity of CrtN2, but more likely due to the asymmetric nature of the diaponeurosporene backbone.

To test this hypothesis, the staphylococcal crtN2 and the *Methylomonas* crtN2 were co-expressed with the staphylococcal crtMN genes, which synthesize diaponeurosporene. The crtM crtN gene cluster was PCR amplified from genomic DNA of *Staphylococcus aureus* NCTC 8325 (ATCC 35556) using forward primer crtM_F/NCTC (5'-qaattcaggaggaataaaccatgacaatgatggatatgaattttaaa-3'; SEQ ID NO:24) and reverse primer crtN_R/NCTC (5'-qaattct-tatacgcccccgctcaatatctt-3'; SEQ ID NO:25). Underlined in the primers are the incorporated EcoRI sites and the bold text indicates an artificial ribosome binding site. The 2410 bp PCR product was first cloned in the pTrcHis2-TOPO cloning vector, resulting in pDCQ165. This 2.4 kb EcoRI fragment from pDCQ165 containing the staphylococcal crtM and crtN genes was ligated into the EcoRI site of pBHR1 vector to create pDCQ166 (Table 2), in which the crtM and crtN genes are expressed under the control of the chloramphenicol resistant gene promoter of pBHR1. The *Methylomonas* 16a crtN2 gene was PCR amplified from its genomic DNA using primer pairs crtN2_F3/16a (SEQ ID NO:26) and crtN2_R/16a (SEQ ID NO:27). The *S. aureus* crtN2 gene was amplified from the genomic DNA of ATCC 35556, using primer pairs crtN2_F/NCTC (SEQ ID NO:28) and crtN2_R/NCTC8325 (SEQ ID NO:23). The 1499 bp *Methylomonas* crtN2 gene and 1498 bp *Staphylococcus* crtN2 gene were cloned into the pTrcHis2-TOPO cloning vector, resulting in plasmid pDCQ167 and pDCQ168, respectively (Table 2). The crtN2 gene on pDCQ167 or pDCQ168 was expressed from the trc promoter on the vector.

TOP10 cells were co-transformed with pDCQ166 plus either pDCQ167 or pDCQ168. The co-transformants were pinkish red, as compared to the yellow color of the transformants of pDCQ166 alone. Cells were grown up in 100 mL LB medium with proper antibiotic at 30° C. for 2 days and harvested by centrifugation. Carotenoids were extracted from the cell pellets first with 10 mL methanol for 30 min and then with 10 mL acetone for 30 min. The extracted pigments were dried under nitrogen and dissolved in 1 mL methanol. Each sample of 0.1 mL was used for HPLC analysis (Table 8).

TABLE 8

Summary of the CrtN2 activity from *Staphylococcus aureus* and *Methylomonas*

| Plasmid | Substrate One end | Functional-ization genes | Elution time (min) | HPLC Spectra (nm) | Carotenoids identified |
|---------|-------------------|--------------------------|--------------------|--------------------|------------------------|
| PDCQ 166 | diapo-neurosporene | None | 14.5 | 415, 438, 467 | 4,4'-diaponeurosporene |
| PDCQ 166 + pDCQ 167 | diapo-neurosporene | crtN2(16a) | 13.8 | 466 | 4,4'-diaponeurosporenal |
| PDCQ 166 + pDCQ168 | diapo-neurosporene | crtN2 (staph) | 13.8 13.3 | 466 396, 418 444 | 4,4'-diaponeurosporenal intermediate |

In the cells containing pDCQ166 alone, diaponeurosporene was synthesized, which has a 7-8 desaturated ψ group at one end and a regular ψ group at the other end. This is consistent with previous reports for crtMN activities (Wieland, B. et al., *J. Bacteriol.* 176:7719–7726 (1994)). When pDCQ167 or pDCQ168 containing *Methylomonas* crtN2 or *Staphylococcus* crtN2 was co-transformed with pDCQ166, a carotenoid with an absorption spectrum of 466 nm was produced. The absorption spectrum and the retention time of this carotenoid suggested it to be 4,4'-diaponeurosporenal with only one end of the diaponeurosporene functionalized. This explained why *S. aureus* produces only one-end functionalized carotenoids (Marshall, J. H., and G. J. Wilmoth. *J. Bacteriol.* 147:900–913 (1981)). Interestingly, *Methylomonas* crtN2 also functionalizes only one end of diaponeurosporene in *E. coli*, in contrast to functionalization of both ends of diapolycopene in *Methylomonas* (Example 1; Kleinig et al., *Z. Naturforsch* 34c, 181–185 (1979); Kleinig and Schmitt, *Z. Naturforsch* 37c, 758–760 (1982)). It is most likely that the desaturated ψ group, present at one end of diaponeurosporene (7-8 desaturated in FIG. 2B) and both ends of diapolycopene (7-8 and 7'-8' desaturated in FIG. 2A), is what is recognized as the preferred substrate by CrtN2 for addition of an omega-aldehyde functional group.

What is claimed is:

1. An isolated nucleic acid molecule selected from the group consisting of:
   a) an isolated nucleic acid molecule encoding a 4,4'-diapocarotene dialdehyde dehydrogenase comprising the amino acid sequence as set forth in SEQ ID NO:6;
   b) an isolated nucleic acid molecule encoding a 4,4'-diapocarotene dialdehyde dehydrogenase that hybridizes with (a) under the following hybridization conditions: 0.1×SSC, 0.1% SDS, 65° C. and washed with 2×SSC, 0.1% SDS followed by 0.1×SSC, 0.1% SDS; and
   c) an isolated nucleic acid molecule that is completely complementary to (a) or (b).

2. The isolated nucleic acid molecule as set forth in SEQ ID NO:5.

3. A chimeric gene comprising the isolated nucleic acid molecule of claim 1 operably linked to suitable regulatory sequences.

4. An isolated transformed host cell comprising the chimeric gene of claim 3.

5. The isolated transformed host cell of claim 4 wherein the host cell is selected from the group consisting of bacteria, yeast, filamentous fungi, algae, and green plants.

6. The isolated transformed host cell of claim 5 wherein the host cell is selected from the group consisting of *Aspergillus, Trichoderma, Saccharomyces, Pichia, Candida, Hansenula, Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Methylobacterium, Alcaligenes, Synechocystis, Synechococcus, Anabaena, Thiobacillus, Methanobacterium, Klebsiella, Myxococcus* and *Staphylococcus*.

7. The isolated transformed host cell of claim 4 wherein the host cell is selected from the group consisting of *Spirulina, Haemotacoccus,* and *Dunalliela*.

8. The isolated transformed host cell of claim 4 wherein the host cell is selected from the group consisting of soybean, rapeseed, pepper, sunflower, cotton, corn, tobacco, alfalfa, wheat, barley, oats, sorghum, rice, *Arabidopsis,* cruciferous vegetables, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

* * * * *

SEQUENCE LISTING

<160> NUMBER OF SEQ ID NOS: 28

<210> SEQ ID NO 1
<211> LENGTH: 1092
<212> TYPE: DNA
<213> ORGANISM: Methylomonas sp.16a

<400> SEQUENCE: 1

```
atgaacggac ctcaaccact cattaccaac ccgcaattgc tttcgcaatt atcagacgcg    60
gaactacagg cagtttact  cgaaggagtc tcacggactt ttgcgctcac cattccccag   120
ctgccggaga atctgtaccc tgccgttgcc aacgcctatt tgttgtgccg tatcgtcgac   180
acgatcgaag acgaaatctc gctgaacgcg aacaaaaaa  aacgttttg  cagcgaattc   240
atccaaatcg tcaaaacagg cgaaggtgct caagcttttg ccgatgaact cgcgccttta   300
cttttcgacac aaaccattcc cgccgaacac agcctgattc atttgatccc tagggtcatt   360
gcgatcacgc acagcctgga tcgggcgcaa attgaagcct tggcttgttg cgtggaaacg   420
atgcgaacg  gcatgccggt ctatcaagcc ctggacctgc gggccggcct gaaaaccatg   480
aaagacatgg atgattactg ttattacgta gccggctgcg tcggagaaat gctggccaag   540
ctgttttgtc actactcgcc gcaaatcgac gcgcatcgcg acgaattact gaagctttcc   600
gtatcattcg gccaaggctt gcaaatgacc aacattctga aagacatctg ggatgatgct   660
cagcgtggcg tgtgctggct gccgcaagac attttcaccg aaaccggctt caacctggcg   720
gacttgacgc caaccaccaa cgacgaacgc tttcgcaaag gactggagca cctgatcagc   780
atcgcgcacg gtcatttgca gaacgccttg acctataccc aattactgcc tcgccacgaa   840
```

```
acgggcattc gcaacttctg cctgtgggcg ctgggcatgg cggtgttgac actgaaaaag    900
atcaagcaaa acctgagctt caacgaatcc agccaggtca agatcagccg gaatagcgtc    960
aaggccacga ttttggcctg caagctcagc gcgcgcagca acctgttact ttcattactt   1020
ttcaatctga ccagccaggg actaaagaca cctggttggc agtacttacc cgaatcgcac   1080
actggacaat aa                                                       1092
```

<210> SEQ ID NO 2
<211> LENGTH: 363
<212> TYPE: PRT
<213> ORGANISM: Methylomonas sp.16a

<400> SEQUENCE: 2

```
Met Asn Gly Pro Gln Pro Leu Ile Thr Asn Pro Gln Leu Leu Ser Gln
1               5                   10                  15

Leu Ser Asp Ala Glu Leu Gln Ala Val Leu Glu Gly Val Ser Arg
            20                  25                  30

Thr Phe Ala Leu Thr Ile Pro Gln Leu Pro Glu Asn Leu Tyr Pro Ala
        35                  40                  45

Val Ala Asn Ala Tyr Leu Leu Cys Arg Ile Val Asp Thr Ile Glu Asp
    50                  55                  60

Glu Ile Ser Leu Asn Ala Glu Gln Lys Lys Arg Phe Cys Ser Glu Phe
65                  70                  75                  80

Ile Gln Ile Val Lys Thr Gly Glu Gly Ala Gln Ala Phe Ala Asp Glu
                85                  90                  95

Leu Ala Pro Leu Leu Ser Thr Gln Thr Ile Pro Ala Glu His Ser Leu
            100                 105                 110

Ile His Leu Ile Pro Arg Val Ile Ala Ile Thr His Ser Leu Asp Arg
        115                 120                 125

Ala Gln Ile Glu Ala Leu Ala Cys Cys Val Glu Thr Met Ala Asn Gly
    130                 135                 140

Met Pro Val Tyr Gln Ala Leu Asp Leu Arg Ala Gly Leu Lys Thr Met
145                 150                 155                 160

Lys Asp Met Asp Asp Tyr Cys Tyr Tyr Val Ala Gly Cys Val Gly Glu
                165                 170                 175

Met Leu Ala Lys Leu Phe Cys His Tyr Ser Pro Gln Ile Asp Ala His
            180                 185                 190

Arg Asp Glu Leu Leu Lys Leu Ser Val Ser Phe Gly Gln Gly Leu Gln
        195                 200                 205

Met Thr Asn Ile Leu Lys Asp Ile Trp Asp Asp Ala Gln Arg Gly Val
    210                 215                 220

Cys Trp Leu Pro Gln Asp Ile Phe Thr Glu Thr Gly Phe Asn Leu Ala
225                 230                 235                 240

Asp Leu Thr Pro Thr Thr Asn Asp Glu Arg Phe Arg Lys Gly Leu Glu
                245                 250                 255

His Leu Ile Ser Ile Ala His Gly His Leu Gln Asn Ala Leu Thr Tyr
            260                 265                 270

Thr Gln Leu Leu Pro Arg His Glu Thr Gly Ile Arg Asn Phe Cys Leu
        275                 280                 285

Trp Ala Leu Gly Met Ala Val Leu Thr Leu Lys Lys Ile Lys Gln Asn
    290                 295                 300

Leu Ser Phe Asn Glu Ser Ser Gln Val Lys Ile Ser Arg Asn Ser Val
305                 310                 315                 320
```

```
Lys Ala Thr Ile Leu Ala Cys Lys Leu Ser Ala Arg Ser Asn Leu Leu
            325                 330                 335

Leu Ser Leu Leu Phe Asn Leu Thr Ser Gln Gly Leu Lys Thr Pro Gly
        340                 345                 350

Trp Gln Tyr Leu Pro Glu Ser His Thr Gly Gln
        355                 360

<210> SEQ ID NO 3
<211> LENGTH: 1536
<212> TYPE: DNA
<213> ORGANISM: Methylomonas sp.16a

<400> SEQUENCE: 3
atggccaaca ccaaacacat catcatcgtc ggcgcgggtc ccggcggact ttgcgccggc      60
atgttgctga gccagcgcgg cttcaaggta tcgattttcg acaaacatgc agaaatcggc    120
ggccgcaacc gcccgatcaa catgaacggc tttaccttcg ataccggtcc gacattcttg    180
ttgatgaaag gcgtgctgga cgaaatgttc gaactgtgcg agcgccgtag cgaggattat    240
ctggaattcc tgccgctaag cccgatgtac cgcctgctgt acgacgaccg cgacatcttc    300
gtctattccg accgcgagaa catgcgcgcc gaattgcaac gggtattcga cgaaggcacg    360
gacggctacg aacagttcat ggaacaggaa cgcaaacgct tcaacgcgct gtatccctgc    420
atcacccgcg attattccag cctgaaatcc ttttgtcgc tggacttgat caaggccctg    480
ccgtggctgg cttttccgaa agcgtgttc aataatctcg ccagtatttt caaccaggaa    540
aaaatgcgcc tggccttttg ctttcagtcc aagtatctgg catgtcgcc gtgggaatgc    600
ccggcactgt ttacgatgct gccctatctg gagcacgaat acggcattta tcacgtcaaa    660
ggcggcctga accgcatcgc ggcggcgatg gcgcaagtga tcgcggaaaa cggcggcgaa    720
attcacttga cagcgaaatc cgagtcgctg atcatcgaaa acggcgctgc caagggcgtc    780
aaattacaac atgcgcgga gctgcgcggc gacgaagtca tcatcaacgc ggattttgcc    840
cacgcgatga cgcatctggt caaaccgggc gtcttgaaaa atacaccccc ggaaaacctg    900
aagcagcgcg agtattcctg ttcgaccttc atgctgtatc tgggtttgga caagatttac    960
gatctgccgc accataccat cgtgtttgcc aaggattaca ccaccaatat ccgcaacatt   1020
ttcgacaaca aaaccctgac ggacgatttt tcgtttacg tgcaaaacgc cagcgccagc   1080
gacgacagcc tagcgccagc cggcaaatcg cgctgtacg tgctggtgcc gatgcccaac   1140
aacgacagcg gcctggactg gcaggcgcat tgccaaaacg tgcgcgaaca ggtgttggac   1200
acgctgggcg cgcgactggg attgagcgac atcagagccc atatcgaatg cgaaaaaatc   1260
atcacgccgc aaacctggga aacggacgaa cacgtttaca agggcgccac tttcagtttg   1320
tcgcacaagt tcagccaaat gctgtactgg cggccgcaca accgtttcga ggaactggcc   1380
aattgctatc tggtcggcgg cggcacgcat cccggtagcg gtttgccgac catctacgaa   1440
tcggcgcgga tttcggccaa gctgatttcc cagaaacatc gggtgaggtt caaggacata   1500
gcacacagcg cctggctgaa aaagccaaa gcctga                             1536

<210> SEQ ID NO 4
<211> LENGTH: 511
<212> TYPE: PRT
<213> ORGANISM: Methylomonas sp.16a

<400> SEQUENCE: 4

Met Ala Asn Thr Lys His Ile Ile Ile Val Gly Ala Gly Pro Gly Gly
1               5                   10                  15
```

```
Leu Cys Ala Gly Met Leu Leu Ser Gln Arg Gly Phe Lys Val Ser Ile
             20                  25                  30

Phe Asp Lys His Ala Glu Ile Gly Gly Arg Asn Arg Pro Ile Asn Met
             35                  40                  45

Asn Gly Phe Thr Phe Asp Thr Gly Pro Thr Phe Leu Leu Met Lys Gly
 50                  55                  60

Val Leu Asp Glu Met Phe Glu Leu Cys Glu Arg Arg Ser Glu Asp Tyr
 65                  70                  75                  80

Leu Glu Phe Leu Pro Leu Ser Pro Met Tyr Arg Leu Leu Tyr Asp Asp
                 85                  90                  95

Arg Asp Ile Phe Val Tyr Ser Asp Arg Glu Asn Met Arg Ala Glu Leu
             100                 105                 110

Gln Arg Val Phe Asp Glu Gly Thr Asp Gly Tyr Glu Gln Phe Met Glu
             115                 120                 125

Gln Glu Arg Lys Arg Phe Asn Ala Leu Tyr Pro Cys Ile Thr Arg Asp
             130                 135                 140

Tyr Ser Ser Leu Lys Ser Phe Leu Ser Leu Asp Leu Ile Lys Ala Leu
145                 150                 155                 160

Pro Trp Leu Ala Phe Pro Lys Ser Val Phe Asn Asn Leu Gly Gln Tyr
                 165                 170                 175

Phe Asn Gln Glu Lys Met Arg Leu Ala Phe Cys Phe Gln Ser Lys Tyr
             180                 185                 190

Leu Gly Met Ser Pro Trp Glu Cys Pro Ala Leu Phe Thr Met Leu Pro
             195                 200                 205

Tyr Leu Glu His Glu Tyr Gly Ile Tyr His Val Lys Gly Gly Leu Asn
 210                 215                 220

Arg Ile Ala Ala Ala Met Ala Gln Val Ile Ala Glu Asn Gly Gly Glu
225                 230                 235                 240

Ile His Leu Asn Ser Glu Ile Glu Ser Leu Ile Ile Glu Asn Gly Ala
                 245                 250                 255

Ala Lys Gly Val Lys Leu Gln His Gly Ala Glu Leu Arg Gly Asp Glu
             260                 265                 270

Val Ile Ile Asn Ala Asp Phe Ala His Ala Met Thr His Leu Val Lys
             275                 280                 285

Pro Gly Val Leu Lys Lys Tyr Thr Pro Glu Asn Leu Lys Gln Arg Glu
 290                 295                 300

Tyr Ser Cys Ser Thr Phe Met Leu Tyr Leu Gly Leu Asp Lys Ile Tyr
305                 310                 315                 320

Asp Leu Pro His His Thr Ile Val Phe Ala Lys Asp Tyr Thr Thr Asn
                 325                 330                 335

Ile Arg Asn Ile Phe Asp Asn Lys Thr Leu Thr Asp Asp Phe Ser Phe
             340                 345                 350

Tyr Val Gln Asn Ala Ser Ala Ser Asp Asp Ser Leu Ala Pro Ala Gly
             355                 360                 365

Lys Ser Ala Leu Tyr Val Leu Val Pro Met Pro Asn Asn Asp Ser Gly
 370                 375                 380

Leu Asp Trp Gln Ala His Cys Gln Asn Val Arg Glu Gln Val Leu Asp
385                 390                 395                 400

Thr Leu Gly Ala Arg Leu Gly Leu Ser Asp Ile Arg Ala His Ile Glu
                 405                 410                 415

Cys Glu Lys Ile Ile Thr Pro Gln Thr Trp Glu Thr Asp Glu His Val
             420                 425                 430
```

-continued

| | | | | | | | | | | | | |
|---|---|---|---|---|---|---|---|---|---|---|---|---|
|Tyr|Lys|Gly|Ala|Thr|Phe|Ser|Leu|Ser|His|Lys|Phe|Ser|Gln|Met|Leu|
| | |435| | | |440| | | |445| | | | | |
|Tyr|Trp|Arg|Pro|His|Asn|Arg|Phe|Glu|Glu|Leu|Ala|Asn|Cys|Tyr|Leu|
| |450| | | | |455| | | | |460| | | | |
|Val|Gly|Gly|Gly|Thr|His|Pro|Gly|Ser|Gly|Leu|Pro|Thr|Ile|Tyr|Glu|
|465| | | | |470| | | | |475| | | | |480|
|Ser|Ala|Arg|Ile|Ser|Ala|Lys|Leu|Ile|Ser|Gln|Lys|His|Arg|Val|Arg|
| | | | |485| | | | |490| | | | |495| |
|Phe|Lys|Asp|Ile|Ala|His|Ser|Ala|Trp|Leu|Lys|Lys|Ala|Lys|Ala| |
| | | |500| | | |505| | | |510| | | | |

<210> SEQ ID NO 5
<211> LENGTH: 1593
<212> TYPE: DNA
<213> ORGANISM: Methylomonas sp.16a

<400> SEQUENCE: 5

| | | |
|---|---|---|
|atgacgacga tagcagccgt ctccccactg gatggccgct tgctgggaca ttttccagtc|  |60|
|agcaagccgg cgctcattca gcaacagctg acaaaatccc gccgcgccgc cctgctttgg|  |120|
|cgcgagctgc cggtcacgga acgggtcaaa cgcctgtcgc ccttgaaaaa acagctgctg|  |180|
|gataacctgg acagactctg cgaaaccatc cgcctcagca ccggcaaggt tcgcaccgag|  |240|
|gccttgctgg gggaaattta ccggtgctg gatttactgg cgtattacca aaagcgggcg|  |300|
|ccgcggattc tacgcacgcg cgccgtgtcc acctcgccgt tcgcgtttcc ggccgccacc|  |360|
|gccccgcatcg aacgccgccc ttacggcgtg gtcgcggtga tctcgccatg gaattacccg|  |420|
|tttcacctga gcgtcgcccc gctgctgacc gctttgctgg ccggcaatgc ggtaatcctg|  |480|
|aaaccctccg aactctgctt gccggtcggt cagttgatcg tcgatttgtt cgccacgctg|  |540|
|gatttgccgg acgggttggt gcaatgggtc atcggcgacg ccaaaccgg cgcggaactg|  |600|
|atagacgccc gccccgatct ggtgtttttc accggcggcc tgcagaccgg tcgggcggtc|  |660|
|atgcaacgcg ccgcccggca tccgattccg gtcatgctgg agttgggcgg taaagacacc|  |720|
|atgctggtgc tggccgacgc cgacctcaag cgcgccagcg ctgccgcgct gtacggcgcg|  |780|
|ttttgcaata gcggccaagt ctgcgtctcg gtcgaacgtc tgtacgtgca acaagcctgt|  |840|
|tttgcggaat tcctggccat gctgctgaag ggcctgtcca agctcaaggt cggccatgac|  |900|
|ccgcacggcg atgtgggagt gatgacgtcc gcccggcaaa tcgacatcgt ccaggcccat|  |960|
|tacgaggacg ccatcgccca gggcgccaag gcctccggcc gctgctgcg cgacggcaat|  |1020|
|gtcgtgcaac ccgtggtgct tgggacgtg caccacggca tgaaggtcat gcgcgaggaa|  |1080|
|accttcggtc cgttgctgcc ggtcatgccg ttcagcgacg aagccgaggc catcaagctc|  |1140|
|gccaacgaca gcgatctggg tctaaacgcc agcatctgga gccaggatat aatcaaggcc|  |1200|
|gagcgccttg ctggacaact agatgtcggc aactgggcga tcaacgacgt attgaaaaac|  |1260|
|gtgggccatt ccggcctgcc cttcggcggc gtcaagcaaa gcgggtttgg ccgttatcac|  |1320|
|ggcgccgaag gcttgctgaa cttcagctac ccggtatcgg gcctgaccaa tcgcagccgc|  |1380|
|ttgcccaaag aacccaactg gttcccttac agcgcatcag gctatgaaaa tttcaagggt|  |1440|
|ttcctcgatt ttatctacgg cgaagactcg atgctgcagc gcggtcgccg caatcagcaa|  |1500|
|gcgctgcaag ccttccgcga gttttccatt tcgattgga cacaacgctg gcaaaacctg|  |1560|
|aaactgctgt tttcttggac acgggatgac taa|  |1593|

<210> SEQ ID NO 6

```
<211> LENGTH: 530
<212> TYPE: PRT
<213> ORGANISM: Methylomonas sp.16a

<400> SEQUENCE: 6

Met Thr Thr Ile Ala Ala Val Ser Pro Leu Asp Gly Arg Leu Leu Gly
1               5                   10                  15

His Phe Pro Val Ser Lys Pro Ala Leu Ile Gln Gln Gln Leu Thr Lys
            20                  25                  30

Ser Arg Arg Ala Ala Leu Leu Trp Arg Glu Leu Pro Val Thr Glu Arg
        35                  40                  45

Val Lys Arg Leu Ser Pro Leu Lys Lys Gln Leu Leu Asp Asn Leu Asp
    50                  55                  60

Arg Leu Cys Glu Thr Ile Arg Leu Ser Thr Gly Lys Val Arg Thr Glu
65                  70                  75                  80

Ala Leu Leu Gly Glu Ile Tyr Pro Val Leu Asp Leu Leu Ala Tyr Tyr
                85                  90                  95

Gln Lys Arg Ala Pro Arg Ile Leu Arg Thr Arg Ala Val Ser Thr Ser
            100                 105                 110

Pro Phe Ala Phe Pro Ala Ala Thr Ala Arg Ile Glu Arg Arg Pro Tyr
        115                 120                 125

Gly Val Val Ala Val Ile Ser Pro Trp Asn Tyr Pro Phe His Leu Ser
130                 135                 140

Val Ala Pro Leu Leu Thr Ala Leu Leu Ala Gly Asn Ala Val Ile Leu
145                 150                 155                 160

Lys Pro Ser Glu Leu Cys Leu Pro Val Gly Gln Leu Ile Val Asp Leu
                165                 170                 175

Phe Ala Thr Leu Asp Leu Pro Asp Gly Leu Val Gln Trp Val Ile Gly
            180                 185                 190

Asp Gly Gln Thr Gly Ala Glu Leu Ile Asp Ala Arg Pro Asp Leu Val
        195                 200                 205

Phe Phe Thr Gly Gly Leu Gln Thr Gly Arg Ala Val Met Gln Arg Ala
210                 215                 220

Ala Arg His Pro Ile Pro Val Met Leu Glu Leu Gly Gly Lys Asp Thr
225                 230                 235                 240

Met Leu Val Leu Ala Asp Ala Asp Leu Lys Arg Ala Ser Ala Ala Ala
                245                 250                 255

Leu Tyr Gly Ala Phe Cys Asn Ser Gly Gln Val Cys Val Ser Val Glu
            260                 265                 270

Arg Leu Tyr Val Gln Gln Ala Cys Phe Ala Glu Phe Leu Ala Met Leu
        275                 280                 285

Leu Lys Gly Leu Ser Lys Leu Lys Val Gly His Asp Pro His Gly Asp
    290                 295                 300

Val Gly Val Met Thr Ser Ala Arg Gln Ile Asp Ile Val Gln Ala His
305                 310                 315                 320

Tyr Glu Asp Ala Ile Ala Gln Gly Ala Lys Ala Ser Gly Pro Leu Leu
                325                 330                 335

Arg Asp Gly Asn Val Val Gln Pro Val Leu Trp Asp Val His His
            340                 345                 350

Gly Met Lys Val Met Arg Glu Glu Thr Phe Gly Pro Leu Leu Pro Val
        355                 360                 365

Met Pro Phe Ser Asp Glu Ala Glu Ala Ile Lys Leu Ala Asn Asp Ser
370                 375                 380

Asp Leu Gly Leu Asn Ala Ser Ile Trp Ser Gln Asp Ile Ile Lys Ala
```

```
                385                 390                 395                 400
            Glu Arg Leu Ala Gly Gln Leu Asp Val Gly Asn Trp Ala Ile Asn Asp
                            405                 410                 415
            Val Leu Lys Asn Val Gly His Ser Gly Leu Pro Phe Gly Val Lys
                        420                 425                 430
            Gln Ser Gly Phe Gly Arg Tyr His Gly Ala Glu Gly Leu Leu Asn Phe
                        435                 440                 445
            Ser Tyr Pro Val Ser Gly Leu Thr Asn Arg Ser Arg Leu Pro Lys Glu
                    450                 455                 460
            Pro Asn Trp Phe Pro Tyr Ser Ala Ser Gly Tyr Glu Asn Phe Lys Gly
            465                 470                 475                 480
            Phe Leu Asp Phe Ile Tyr Gly Glu Asp Ser Met Leu Gln Arg Gly Arg
                            485                 490                 495
            Arg Asn Gln Gln Ala Leu Gln Ala Phe Arg Glu Phe Ser Ile Phe Asp
                        500                 505                 510
            Trp Thr Gln Arg Trp Gln Asn Leu Lys Leu Leu Phe Ser Trp Thr Arg
                        515                 520                 525
            Asp Asp
                530

<210> SEQ ID NO 7
<211> LENGTH: 1494
<212> TYPE: DNA
<213> ORGANISM: Methylomonas sp.16a

<400> SEQUENCE: 7
atgaactcaa atgacaacca acgcgtgatc gtgatcggcg ccggcctcgg cggcctgtcc      60
gccgctattt cgctggccac ggccggcttt tccgtgcaac tcatcgaaaa aaacgacaag     120
gtcggcggca agctcaacat catgaccaaa gacggcttta ccttcgatct ggggccgtcc     180
attttgacga tgccgcacat ctttgaggcc ttgttcacag gggccggcaa aaacatggcc     240
gattacgtgc aaatccagaa agtcgaaccg cactggcgca atttcttcga ggacggtagc     300
gtgatcgact tgtgcgaaga cgccgaaacc cagcgccgcg agctggataa acttggcccc     360
ggcacttacg cgcaattcca gcgctttctg gactattcga aaaacctctg cacggaaacc     420
gaagccggtt acttcgccaa gggcctggac ggcttttggg attactcaa gttttacggc     480
ccgctccgca gcctgctgag tttcgacgtc ttccgcagca tggaccaggg cgtgcgccgc     540
tttatttccg atcccaagtt ggtcgaaatc ctgaattact tcatcaaata cgtcggctcc     600
tcgccttacg atgcgcccgc cttgatgaac ctgctgcctt acattcaata tcattacggc     660
ctgtggtacg tgaaaggcgg catgtatggc atggcgcagg ccatggaaaa actggccgtg     720
gaattgggcg tcgagattcg tttagatgcc gaggtgtcgg aaatccaaaa acaggacggc     780
agagcctgcg ccgtaaagtt ggcgaacggc gacgtgctgc cggccgacat cgtggtgtcg     840
aacatggaag tgattccggc gatggaaaaa ctgctgcgca gcccggccag cgaactgaaa     900
aaaatgcagc gcttcgagcc tagctgttcc ggcctggtgc tgcacttggg cgtggacagg     960
ctgtatccgc aactggcgca ccacaatttc ttttattccg atcatccgcg cgaacatttc    1020
gatgcggtat tcaaaagcca tcgcctgtcg acgatccga ccatttatct ggtcgcgccg    1080
tgcaagaccg accccgccca ggcgccggcc ggctgcgaga tcatcaaaat cctgccccat    1140
atcccgcacc tcgaccccga caaactgctg accgccgagg attattcagc cttgcgcgag    1200
cgggtgctgg tcaaactcga acgcatgggc ctgacggatt tacgccaaca catcgtgacc    1260
```

-continued

```
gaagaatact ggacgccgct ggatattcag gccaaatatt attcaaacca gggctcgatt    1320
tacggcgtgg tcgccgaccg cttcaaaaac ctgggtttca aggcacctca acgcagcagc    1380
gaattatcca atctgtattt cgtcggcggc agcgtcaatc ccggcggcgg catgccgatg    1440
gtgacgctgt ccgggcaatt ggtgagggac aagattgtgg cggatttgca ataa          1494
```

<210> SEQ ID NO 8
<211> LENGTH: 497
<212> TYPE: PRT
<213> ORGANISM: Methylomonas sp.16a

<400> SEQUENCE: 8

```
Met Asn Ser Asn Asp Asn Gln Arg Val Ile Val Ile Gly Ala Gly Leu
1               5                   10                  15

Gly Gly Leu Ser Ala Ala Ile Ser Leu Ala Thr Ala Gly Phe Ser Val
            20                  25                  30

Gln Leu Ile Glu Lys Asn Asp Lys Val Gly Gly Lys Leu Asn Ile Met
        35                  40                  45

Thr Lys Asp Gly Phe Thr Phe Asp Leu Gly Pro Ser Ile Leu Thr Met
    50                  55                  60

Pro His Ile Phe Glu Ala Leu Phe Thr Gly Ala Gly Lys Asn Met Ala
65                  70                  75                  80

Asp Tyr Val Gln Ile Gln Lys Val Glu Pro His Trp Arg Asn Phe Phe
                85                  90                  95

Glu Asp Gly Ser Val Ile Asp Leu Cys Glu Asp Ala Glu Thr Gln Arg
            100                 105                 110

Arg Glu Leu Asp Lys Leu Gly Pro Gly Thr Tyr Ala Gln Phe Gln Arg
        115                 120                 125

Phe Leu Asp Tyr Ser Lys Asn Leu Cys Thr Glu Thr Glu Ala Gly Tyr
    130                 135                 140

Phe Ala Lys Gly Leu Asp Gly Phe Trp Asp Leu Leu Lys Phe Tyr Gly
145                 150                 155                 160

Pro Leu Arg Ser Leu Leu Ser Phe Asp Val Phe Arg Ser Met Asp Gln
                165                 170                 175

Gly Val Arg Arg Phe Ile Ser Asp Pro Lys Leu Val Glu Ile Leu Asn
            180                 185                 190

Tyr Phe Ile Lys Tyr Val Gly Ser Ser Pro Tyr Asp Ala Pro Ala Leu
        195                 200                 205

Met Asn Leu Leu Pro Tyr Ile Gln Tyr His Tyr Gly Leu Trp Tyr Val
    210                 215                 220

Lys Gly Gly Met Tyr Gly Met Ala Gln Ala Met Glu Lys Leu Ala Val
225                 230                 235                 240

Glu Leu Gly Val Glu Ile Arg Leu Asp Ala Glu Val Ser Glu Ile Gln
                245                 250                 255

Lys Gln Asp Gly Arg Ala Cys Ala Val Lys Leu Ala Asn Gly Asp Val
            260                 265                 270

Leu Pro Ala Asp Ile Val Val Ser Asn Met Glu Val Ile Pro Ala Met
        275                 280                 285

Glu Lys Leu Leu Arg Ser Pro Ala Ser Glu Leu Lys Lys Met Gln Arg
    290                 295                 300

Phe Glu Pro Ser Cys Ser Gly Leu Val Leu His Leu Gly Val Asp Arg
305                 310                 315                 320

Leu Tyr Pro Gln Leu Ala His His Asn Phe Phe Tyr Ser Asp His Pro
                325                 330                 335
```

```
Arg Glu His Phe Asp Ala Val Phe Lys Ser His Arg Leu Ser Asp Asp
                340                 345                 350

Pro Thr Ile Tyr Leu Val Ala Pro Cys Lys Thr Asp Pro Ala Gln Ala
            355                 360                 365

Pro Ala Gly Cys Glu Ile Ile Lys Ile Leu Pro His Ile Pro His Leu
        370                 375                 380

Asp Pro Asp Lys Leu Leu Thr Ala Glu Asp Tyr Ser Ala Leu Arg Glu
385                 390                 395                 400

Arg Val Leu Val Lys Leu Glu Arg Met Gly Leu Thr Asp Leu Arg Gln
                405                 410                 415

His Ile Val Thr Glu Glu Tyr Trp Thr Pro Leu Asp Ile Gln Ala Lys
            420                 425                 430

Tyr Tyr Ser Asn Gln Gly Ser Ile Tyr Gly Val Val Ala Asp Arg Phe
        435                 440                 445

Lys Asn Leu Gly Phe Lys Ala Pro Gln Arg Ser Ser Glu Leu Ser Asn
    450                 455                 460

Leu Tyr Phe Val Gly Gly Ser Val Asn Pro Gly Gly Met Pro Met
465                 470                 475                 480

Val Thr Leu Ser Gly Gln Leu Val Arg Asp Lys Ile Val Ala Asp Leu
                485                 490                 495

Gln

<210> SEQ ID NO 9
<211> LENGTH: 864
<212> TYPE: DNA
<213> ORGANISM: Staphylococcus aureus

<400> SEQUENCE: 9
atgacaatga tggatatgaa ttttaaatat tgtcataaaa tcatgaagaa acattcaaaa      60 agctttctt acgcttttga cttgttacca gaagatcaaa gaaaagcggt ttgggcaatt     120
tatgctgtgt gtcgtaaaat tgatgacagt atagatgttt atggcgatat tcaattttta     180
aatcaaataa agaagatat acaatctatt gaaaaatacc catatgaaca tcatcacttt     240
caaagtgatc gtagaatcat gatggcgctt cagcatgttg cacaacataa aaatatcgcc     300
tttcaatctt tttataatct cattgatact gtatataaag atcaacattt tacaatgttt     360
gaaacggacg ctgaattatt cggatattgt tatggtgttg ctggtacagt aggtgaagta     420
ttgacgccga ttttaagtga tcatgaaaca catcagacat acgatgtcgc aagaagactt     480
ggtgaatcgt tgcaattgat taatatatta agagatgtcg gtgaagattt tgacaatgaa     540
cggatatatt ttagtaagca acgattaaag caatatgaag ttgatattgc tgaagtgtac     600
caaaatggtg ttaataatca ttatattgac ttatgggaat attatgcagc tatcgcagaa     660
aaagattttc aagatgttat ggatcaaatc aaagtattta gtattgaagc acaaccaatc     720
atagaattag cagcacgtat atatattgaa atactggacg aagtgagaca ggctaactat     780
acattacatg aacgtgtttt tgtggataag aggaaaaagg caagttgtt tcatgaaata     840 aatagtaaat atcatagaat atag                                            864

<210> SEQ ID NO 10
<211> LENGTH: 287
<212> TYPE: PRT
<213> ORGANISM: Staphylococcus aureus

<400> SEQUENCE: 10

Met Thr Met Met Asp Met Asn Phe Lys Tyr Cys His Lys Ile Met Lys
```

```
                1               5                    10                   15
Lys His Ser Lys Ser Phe Ser Tyr Ala Phe Asp Leu Leu Pro Glu Asp
                        20                   25                   30

Gln Arg Lys Ala Val Trp Ala Ile Tyr Ala Val Cys Arg Lys Ile Asp
                35                   40                   45

Asp Ser Ile Asp Val Tyr Gly Asp Ile Gln Phe Leu Asn Gln Ile Lys
            50                   55                   60

Glu Asp Ile Gln Ser Ile Glu Lys Tyr Pro Tyr Glu His His His Phe
65                      70                   75                   80

Gln Ser Asp Arg Arg Ile Met Met Ala Leu Gln His Val Ala Gln His
                    85                   90                   95

Lys Asn Ile Ala Phe Gln Ser Phe Tyr Asn Leu Ile Asp Thr Val Tyr
                100                  105                  110

Lys Asp Gln His Phe Thr Met Phe Glu Thr Asp Ala Glu Leu Phe Gly
                115                  120                  125

Tyr Cys Tyr Gly Val Ala Gly Thr Val Gly Glu Val Leu Thr Pro Ile
        130                  135                  140

Leu Ser Asp His Glu Thr His Gln Thr Tyr Asp Val Ala Arg Arg Leu
145                 150                  155                  160

Gly Glu Ser Leu Gln Leu Ile Asn Ile Leu Arg Asp Val Gly Glu Asp
                    165                  170                  175

Phe Asp Asn Glu Arg Ile Tyr Phe Ser Lys Gln Arg Leu Lys Gln Tyr
                180                  185                  190

Glu Val Asp Ile Ala Glu Val Tyr Gln Asn Gly Val Asn Asn His Tyr
                195                  200                  205

Ile Asp Leu Trp Glu Tyr Tyr Ala Ala Ile Ala Glu Lys Asp Phe Gln
210                 215                  220

Asp Val Met Asp Gln Ile Lys Val Phe Ser Ile Glu Ala Gln Pro Ile
225                 230                  235                  240

Ile Glu Leu Ala Ala Arg Ile Tyr Ile Glu Ile Leu Asp Glu Val Arg
                245                  250                  255

Gln Ala Asn Tyr Thr Leu His Glu Arg Val Phe Val Asp Lys Arg Lys
                260                  265                  270

Lys Ala Lys Leu Phe His Glu Ile Asn Ser Lys Tyr His Arg Ile
                275                  280                  285
```

<210> SEQ ID NO 11
<211> LENGTH: 1509
<212> TYPE: DNA
<213> ORGANISM: Staphylococcus aureus

<400> SEQUENCE: 11

```
atgaagattg cagtaattgg tgcaggtgtc acaggattag cagcggcagc ccgtattgct    60
tctcaaggtc atgaagtgac gatatttgaa aaaataataa tgtaggcgg gcgtatgaat    120
caattaaaga aagacggctt acatttgat atgggtccca caattgtcat gatgccagat    180
gtttataaag atgttttac agcgtgtggt aaaaattatg aagattatat tgaattgaga    240
caattacgtt atatttacga tgtgtatttt gaccacgatg atcgtataac ggtgcctaca    300
gatttagctg aattacagca aatgctagaa agtatagaac ctggttcaac gcatggtttt    360
atgtcctttt taacggatgt ttataaaaaa tatgaaattg cacgtcgcta tttcttagaa    420
agaacgtatc gcaaaccgag tgactttat aatatgacgt cacttgtgca aggtgctaag    480
ttaaaaacgt taaatcatgc agatcagcta attgaacatt atattgataa cgaaaagata    540
```

-continued

```
caaaagcttt tagcgtttca aacgttatac ataggaattg atccaaaacg aggcccgtca       600
ctatattcaa ttattcctat gattgaaatg atgtttggtg tgcattttat taaaggcggt       660
atgtatggca tggctcaagg gctagcgcaa ttaaataaag acttaggcgt taatattgaa       720
ctaaatgctg aaattgagca aattattatt gatcctaaat tcaaacgggc cgatgcgata       780
aaagtgaatg gtgacataag aaaatttgat aaaattttat gtacggctga tttccctagt       840
gttgcggaat cattaatgcc agattttgca cctattaaaa gtatccacc acataaaatt        900 gcagacttag attactcttg ttcagcattt ttaatgtata tcggtataga tattgatgtg       960
acagatcaag tgagacttca taatgttatt ttttcagatg actttagagg caatattgaa      1020
gaaatatttg agggacgttt atcatatgat ccttctattt atgtgtatgt accagcggtc      1080
gctgataaat cacttgcgcc agaaggcaaa actggtattt atgtgctaat gccgacgccg      1140
gaacttaaaa caggtagcgg aatcgattgg tcagatgaag ctttgacgca acaaataaag      1200
gaaattattt atcgtaaatt agcaacgatt gaagtatttg aagatataaa atcgcatatt      1260
gtttcagaaa caatctttac gccaaatgat tttgagcaaa cgtatcatgc gaaatttggt      1320
tcggcattcg gtttaatgcc aactttagcg caaagtaatt attatcgtcc acaaaatgta      1380
tcgcgagatt ataaagattt atattttgca ggtgcaagta cgcatccagg tgcaggcgtt      1440
cctattgtct taacgagtgc gaaaataact gtagatgaaa tgattaaaga tattgagcgg      1500
ggcgtataa                                                              1509
```

<210> SEQ ID NO 12
<211> LENGTH: 502
<212> TYPE: PRT
<213> ORGANISM: Staphylococcus aureus

<400> SEQUENCE: 12

```
Met Lys Ile Ala Val Ile Gly Ala Gly Val Thr Gly Leu Ala Ala Ala
1               5                   10                  15

Ala Arg Ile Ala Ser Gln Gly His Glu Val Thr Ile Phe Glu Lys Asn
            20                  25                  30

Asn Asn Val Gly Gly Arg Met Asn Gln Leu Lys Lys Asp Gly Phe Thr
        35                  40                  45

Phe Asp Met Gly Pro Thr Ile Val Met Met Pro Asp Val Tyr Lys Asp
    50                  55                  60

Val Phe Thr Ala Cys Gly Lys Asn Tyr Glu Asp Tyr Ile Glu Leu Arg
65                  70                  75                  80

Gln Leu Arg Tyr Ile Tyr Asp Val Tyr Phe Asp His Asp Arg Ile
                85                  90                  95

Thr Val Pro Thr Asp Leu Ala Glu Leu Gln Gln Met Leu Glu Ser Ile
                100                 105                 110

Glu Pro Gly Ser Thr His Gly Phe Met Ser Phe Leu Thr Asp Val Tyr
            115                 120                 125

Lys Lys Tyr Glu Ile Ala Arg Arg Tyr Phe Leu Glu Arg Thr Tyr Arg
        130                 135                 140

Lys Pro Ser Asp Phe Tyr Asn Met Thr Ser Leu Val Gln Gly Ala Lys
145                 150                 155                 160

Leu Lys Thr Leu Asn His Ala Asp Gln Leu Ile Glu His Tyr Ile Asp
                165                 170                 175

Asn Glu Lys Ile Gln Lys Leu Leu Ala Phe Gln Thr Leu Tyr Ile Gly
            180                 185                 190

Ile Asp Pro Lys Arg Gly Pro Ser Leu Tyr Ser Ile Ile Pro Met Ile
```

```
                195                 200                 205
Glu Met Met Phe Gly Val His Phe Ile Lys Gly Met Tyr Gly Met
    210                 215                 220

Ala Gln Gly Leu Ala Gln Leu Asn Lys Asp Leu Gly Val Asn Ile Glu
225                 230                 235                 240

Leu Asn Ala Glu Ile Glu Gln Ile Ile Asp Pro Lys Phe Lys Arg
                245                 250                 255

Ala Asp Ala Ile Lys Val Asn Gly Asp Ile Arg Lys Phe Asp Lys Ile
                260                 265                 270

Leu Cys Thr Ala Asp Phe Pro Ser Val Ala Glu Ser Leu Met Pro Asp
    275                 280                 285

Phe Ala Pro Ile Lys Lys Tyr Pro Pro His Lys Ile Ala Asp Leu Asp
    290                 295                 300

Tyr Ser Cys Ser Ala Phe Leu Met Tyr Ile Gly Ile Asp Ile Asp Val
305                 310                 315                 320

Thr Asp Gln Val Arg Leu His Asn Val Ile Phe Ser Asp Phe Arg
                325                 330                 335

Gly Asn Ile Glu Glu Ile Phe Glu Gly Arg Leu Ser Tyr Asp Pro Ser
                340                 345                 350

Ile Tyr Val Tyr Val Pro Ala Val Ala Asp Lys Ser Leu Ala Pro Glu
                355                 360                 365

Gly Lys Thr Gly Ile Tyr Val Leu Met Pro Thr Pro Glu Leu Lys Thr
    370                 375                 380

Gly Ser Gly Ile Asp Trp Ser Asp Glu Ala Leu Thr Gln Gln Ile Lys
385                 390                 395                 400

Glu Ile Ile Tyr Arg Lys Leu Ala Thr Ile Glu Val Phe Glu Asp Ile
                405                 410                 415

Lys Ser His Ile Val Ser Glu Thr Ile Phe Thr Pro Asn Asp Phe Glu
                420                 425                 430

Gln Thr Tyr His Ala Lys Phe Gly Ser Ala Phe Gly Leu Met Pro Thr
                435                 440                 445

Leu Ala Gln Ser Asn Tyr Tyr Arg Pro Gln Asn Val Ser Arg Asp Tyr
450                 455                 460

Lys Asp Leu Tyr Phe Ala Gly Ala Ser Thr His Pro Gly Ala Gly Val
465                 470                 475                 480

Pro Ile Val Leu Thr Ser Ala Lys Ile Thr Val Asp Glu Met Ile Lys
                485                 490                 495

Asp Ile Glu Arg Gly Val
            500

<210> SEQ ID NO 13
<211> LENGTH: 1494
<212> TYPE: DNA
<213> ORGANISM: Staphylococcus aureus

<400> SEQUENCE: 13
atgactaaac atatcatcgt tattggtggt ggcttaggtg ggatttctgc agcaattcga      60
atggcacaaa gtggctattc ggtctcatta tatgaacaaa ataatcatat aggaggcaaa     120
gtgaatcgtc atgaatcaga tggctttggc tttgatttag gtccatctat tttaacgatg     180
ccttatattt ttgaaaaatt attcgaatat agcaagaagc aaatgtcaga ctacgttaca     240
atcaagcgat tgccacatca atggcgtagc ttttttccag atggaacgac tatcgatttg     300
tatgaaggta ttaaagaaac aggtcagcat aatgcgatat tgtcgaaaca ggatatagag     360
```

-continued

```
gaactgcaaa attatttgaa ttatacaaga cgaatcgatc gtattactga aaaagggtat      420
ttcaactatg gtttagatac actatctcaa attattaaat ttcatgggcc attaaatgct      480
cttattaatt atgattatgt acatactatg caacaggcca tagacaagcg tatctcgaat      540
ccatacttgc gacaaatgtt aggctatttt atcaaatatg taggttcttc atcatacgat      600
gcgccagctg tattatctat gttattccat atgcaacaag agcaaggcct ttggtatgta      660
gaaggtggaa tccatcattt agccaatgcc ttggaaaagc tagcgcgtga agaaggtgtc      720
acaattcata caggtgcacg tgtggacaat attaaaacat atcaaagacg tgtgacgggt      780
gtcagattag atacaggtga gtttgtaaag gcagattata ttatttcaaa tatggaagtc      840
atacctactt ataaatattt aattcacctt gatactcaac gattaaacaa attagagagg      900
gaatttgagc cggcaagctc aggatatgtg atgcatttag tgttgcttg ccaatacccg       960 caattagcac atcataattt ctttttttacg gaaaatgctt atctcaatta tcaacaagtt     1020
tttcatgaaa aggtattgcc agatgatccg accatttatc tagtaaatac gaataaaact     1080
gatcacacac aagcgccagt aggttatgaa aatatcaaag tcttaccaca tattccatat     1140
attcaagatc agccttttac cactgaagat tatgcgaagt ttagggataa aattttggat     1200
aaattagaaa aatgggact tactgattta agaaaacaca ttatttatga agatgtttgg      1260
acaccggagg atattgaaaa aaattatcgt tctaatcgtg gtgcaatata tggtgttgta     1320
gcagataaaa agaaaaacaa aggatttaaa tttcctaaag aaagtcagta ttttgaaaac     1380
ttgtactttg taggtggatc agtaaatcct ggtggtggca tgccaatggt tacattaagt     1440
gggcaacaag tcgcagacaa aataaacgcg cgagaagcga agaataggaa gtga           1494
```

<210> SEQ ID NO 14
<211> LENGTH: 497
<212> TYPE: PRT
<213> ORGANISM: Staphylococcus aureus

<400> SEQUENCE: 14

```
Met Thr Lys His Ile Ile Val Ile Gly Gly Gly Leu Gly Gly Ile Ser
1               5                   10                  15

Ala Ala Ile Arg Met Ala Gln Ser Gly Tyr Ser Val Ser Leu Tyr Glu
            20                  25                  30

Gln Asn Asn His Ile Gly Gly Lys Val Asn Arg His Glu Ser Asp Gly
        35                  40                  45

Phe Gly Phe Asp Leu Gly Pro Ser Ile Leu Thr Met Pro Tyr Ile Phe
    50                  55                  60

Glu Lys Leu Phe Glu Tyr Ser Lys Lys Gln Met Ser Asp Tyr Val Thr
65                  70                  75                  80

Ile Lys Arg Leu Pro His Gln Trp Arg Ser Phe Pro Asp Gly Thr
                85                  90                  95

Thr Ile Asp Leu Tyr Glu Gly Ile Lys Glu Thr Gly Gln His Asn Ala
            100                 105                 110

Ile Leu Ser Lys Gln Asp Ile Glu Glu Leu Gln Asn Tyr Leu Asn Tyr
        115                 120                 125

Thr Arg Arg Ile Asp Arg Ile Thr Glu Lys Gly Tyr Phe Asn Tyr Gly
    130                 135                 140

Leu Asp Thr Leu Ser Gln Ile Ile Lys Phe His Gly Pro Leu Asn Ala
145                 150                 155                 160

Leu Ile Asn Tyr Asp Tyr Val His Thr Met Gln Gln Ala Ile Asp Lys
                165                 170                 175
```

```
Arg Ile Ser Asn Pro Tyr Leu Arg Gln Met Leu Gly Tyr Phe Ile Lys
                180                 185                 190

Tyr Val Gly Ser Ser Tyr Asp Ala Pro Ala Val Leu Ser Met Leu
            195                 200                 205

Phe His Met Gln Gln Glu Gln Gly Leu Trp Tyr Val Glu Gly Gly Ile
    210                 215                 220

His His Leu Ala Asn Ala Leu Glu Lys Leu Ala Arg Glu Gly Val
225                 230                 235                 240

Thr Ile His Thr Gly Ala Arg Val Asp Asn Ile Lys Thr Tyr Gln Arg
                245                 250                 255

Arg Val Thr Gly Val Arg Leu Asp Thr Gly Glu Phe Val Lys Ala Asp
            260                 265                 270

Tyr Ile Ile Ser Asn Met Glu Val Ile Pro Thr Tyr Lys Tyr Leu Ile
            275                 280                 285

His Leu Asp Thr Gln Arg Leu Asn Lys Leu Glu Arg Glu Phe Glu Pro
    290                 295                 300

Ala Ser Ser Gly Tyr Val Met His Leu Gly Val Ala Cys Gln Tyr Pro
305                 310                 315                 320

Gln Leu Ala His His Asn Phe Phe Thr Glu Asn Ala Tyr Leu Asn
                325                 330                 335

Tyr Gln Gln Val Phe His Glu Lys Val Leu Pro Asp Pro Thr Ile
            340                 345                 350

Tyr Leu Val Asn Thr Asn Lys Thr Asp His Thr Gln Ala Pro Val Gly
                355                 360                 365

Tyr Glu Asn Ile Lys Val Leu Pro His Ile Pro Tyr Ile Gln Asp Gln
            370                 375                 380

Pro Phe Thr Thr Glu Asp Tyr Ala Lys Phe Arg Asp Lys Ile Leu Asp
385                 390                 395                 400

Lys Leu Glu Lys Met Gly Leu Thr Asp Leu Arg Lys His Ile Ile Tyr
                405                 410                 415

Glu Asp Val Trp Thr Pro Glu Asp Ile Glu Lys Asn Tyr Arg Ser Asn
            420                 425                 430

Arg Gly Ala Ile Tyr Gly Val Val Ala Asp Lys Lys Asn Lys Gly
            435                 440                 445

Phe Lys Phe Pro Lys Glu Ser Gln Tyr Phe Glu Asn Leu Tyr Phe Val
    450                 455                 460

Gly Gly Ser Val Asn Pro Gly Gly Met Pro Met Val Thr Leu Ser
465                 470                 475                 480

Gly Gln Gln Val Ala Asp Lys Ile Asn Ala Arg Glu Ala Lys Asn Arg
                485                 490                 495
Lys

<210> SEQ ID NO 15
<211> LENGTH: 27
<212> TYPE: DNA
<213> ORGANISM: Staphylococcus aureus ATCC 35556

<400> SEQUENCE: 15
atgacaatga tggatatgaa tttttaaa                                27

<210> SEQ ID NO 16
<211> LENGTH: 35
<212> TYPE: DNA
<213> ORGANISM: Staphylococcus aureus ATCC 35556

<400> SEQUENCE: 16
```

-continued

```
<210> SEQ ID NO 17
<211> LENGTH: 20
<212> TYPE: DNA
<213> ORGANISM: Methylomonas sp.16a

<400> SEQUENCE: 17
atgaacggac ctcaaccact                                              20

<210> SEQ ID NO 18
<211> LENGTH: 27
<212> TYPE: DNA
<213> ORGANISM: Methylomonas sp.16a

<400> SEQUENCE: 18
ggatccttat tgtccagtgt gcgattc                                      27

<210> SEQ ID NO 19
<211> LENGTH: 36
<212> TYPE: DNA
<213> ORGANISM: Methylomonas sp.16a

<400> SEQUENCE: 19
ggtctcaaat tgcatcaacg gatcatcatg gccaac                            36

<210> SEQ ID NO 20
<211> LENGTH: 44
<212> TYPE: DNA
<213> ORGANISM: Methylomonas sp.16a

<400> SEQUENCE: 20
ggtctctaat tgctagctta ttgcaaatcc gccacaatct tgtc                   44

<210> SEQ ID NO 21
<211> LENGTH: 28
<212> TYPE: DNA
<213> ORGANISM: Artificial sequence
<220> FEATURE:
<223> OTHER INFORMATION: Primer

<400> SEQUENCE: 21
ttattgcaaa tccgccacaa tcttgtcc                                     28

<210> SEQ ID NO 22
<211> LENGTH: 25
<212> TYPE: DNA
<213> ORGANISM: Staphylococcus aureus NCTC 8325

<400> SEQUENCE: 22
gaattcgaag aggtgaacgt catga                                        25

<210> SEQ ID NO 23
<211> LENGTH: 27
<212> TYPE: DNA
<213> ORGANISM: Staphylococcus aureus NCTC 8325

<400> SEQUENCE: 23
gaattcactt cctattcttc gcttctc                                      27

<210> SEQ ID NO 24
<211> LENGTH: 47
<212> TYPE: DNA
<213> ORGANISM: Staphylococcus aureus NCTC 8325
```

(first line continued from previous page:)

ggatcctata ttctatgata tttactattt atttc                             35

```
<400> SEQUENCE: 24
gaattcagga ggaataaacc atgacaatga tggatatgaa ttttaaa                47

<210> SEQ ID NO 25
<211> LENGTH: 29
<212> TYPE: DNA
<213> ORGANISM: Staphylococcus aureus NCTC 8325

<400> SEQUENCE: 25
gaattcttat acgccccgct caatatctt                                    29

<210> SEQ ID NO 26
<211> LENGTH: 23
<212> TYPE: DNA
<213> ORGANISM: Methylomonas sp.16a

<400> SEQUENCE: 26
atgaactcaa atgacaacca acg                                          23

<210> SEQ ID NO 27
<211> LENGTH: 28
<212> TYPE: DNA
<213> ORGANISM: Methylomonas sp.16a

<400> SEQUENCE: 27
gaattctatt gcaaatccgc cacaatct                                     28

<210> SEQ ID NO 28
<211> LENGTH: 25
<212> TYPE: DNA
<213> ORGANISM: Staphylococcus aureus NCTC 8325

<400> SEQUENCE: 28
atgactaaac atatcatcgt tattg                                        25
```